(12) United States Patent
Fidock

(10) Patent No.: US 7,091,024 B2
(45) Date of Patent: Aug. 15, 2006

(54) ENZYME PDE XVI

(75) Inventor: Mark D. Fidock, Sandwich (GB)

(73) Assignee: Pfizer Inc., New York, NY (US)

( * ) Notice: Subject to any disclaimer, the term of this patent is extended or adjusted under 35 U.S.C. 154(b) by 276 days.

(21) Appl. No.: 10/781,181

(22) Filed: Feb. 18, 2004

(65) Prior Publication Data

US 2004/0137508 A1 Jul. 15, 2004

Related U.S. Application Data

(63) Continuation of application No. 09/471,459, filed on Dec. 22, 1999, now abandoned.

(51) Int. Cl.
*C12N 9/16* (2006.01)
*C07H 21/04* (2006.01)

(52) U.S. Cl. .......... 435/196; 435/252.3; 435/320.1; 536/23.2

(58) Field of Classification Search ........ 435/196, 435/252.3, 320.1; 536/23.2
See application file for complete search history.

(56) References Cited

U.S. PATENT DOCUMENTS

| 5,527,896 A | 6/1996 | Wigler et al. ............ 536/23.5 |
| 6,146,876 A | 11/2000 | Robision et al. ............ 435/243 |

FOREIGN PATENT DOCUMENTS

| WO | WO 9735989 | 10/1997 |
| WO | WO 0077226 | 12/2000 |

OTHER PUBLICATIONS

Beavo, et al., *Physiological Reviews*, Cyclic Nucleotide Phosphodiesterases: Functional implications of multiple isoforms, vol. 75(4): 725-748, 1995.
Bloom, et al., *Proc. Natl. Acad. Sci. USA*, Identification and tissue-specific expression of PDE7 phosphodiesterase splice variants, vol. 99: 14188-14192, 1996.
Database EMBL, Accession No. L 12052: Michaeli T. '*Homo sapiens cAMP phosphodiesterase PDE7 (PDE7A1) mRNA, complete cds.*', Mar. 9, 1993.
Database EMBL, Accession No. U68171: Bloom T.J. and Beavo J.A. '*Mus musculus cyclic nucleotide phosphodiesterase PDE7A2 (MMPDE7A) mRNA, complete cds.*', Sep. 20, 1996.
Database EMBL, Accession No. Q13946: '*High-affinity cAMP-specific 3',5'-cyclic phosphodiesterase 7A*', Jul. 15, 1998.
Han, et al., *Journal of Biological Chemistry*, Alternative splicing of the high affinity cAMP-specific phosphodiesterase (PDE7A) mRNA in human skeletal muscle and heart, vol. 272(26): 16152-16157, 1997.
Michaeli, et al., *Journal of Biological Chemistry*, Isolation and characterization of a previously undetected human cAMP phosphodiesterase by complementation of cAMP phosphodiesterase-deficient saccharomyces cerevisiae, vol. 268(17): 12925-12932, 1993.
Nucleotide sequence database EMBL ID AI006099, Accession No. AI006099 Jun. 15, 1998, XP002105162.

*Primary Examiner*—Tekchand Saidha
(74) *Attorney, Agent, or Firm*—Gregg C. Benson; Nicholas I. Slepchuk

(57) ABSTRACT

Amino acid sequences and nucleotide sequences relating to PDE_XIV are described. In a preferred aspect, the amino acid sequences comprise the sequence presented as SEQ ID NO:1 or SEQ ID NO:3 or SEQ ID NO:5.

6 Claims, 9 Drawing Sheets

Figure 1:
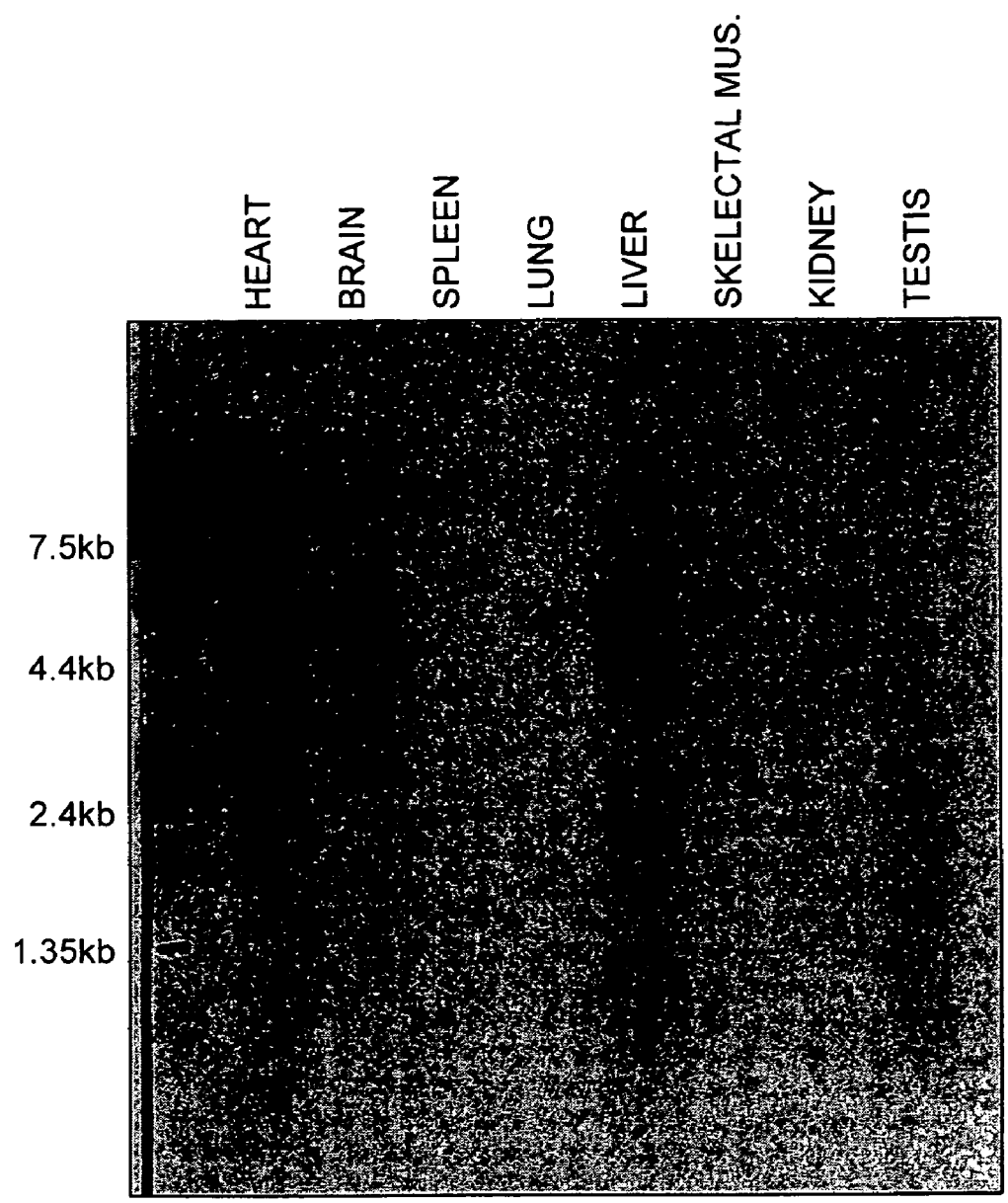

MURINE MTN BLOT PROBED WITH
$^{32}$P-LABELLED MURINE PDE_XIV

MURINE EMBRYO MTN BLOT PROBED
WITH 32P-LABELLED MURINE PDE_XIV

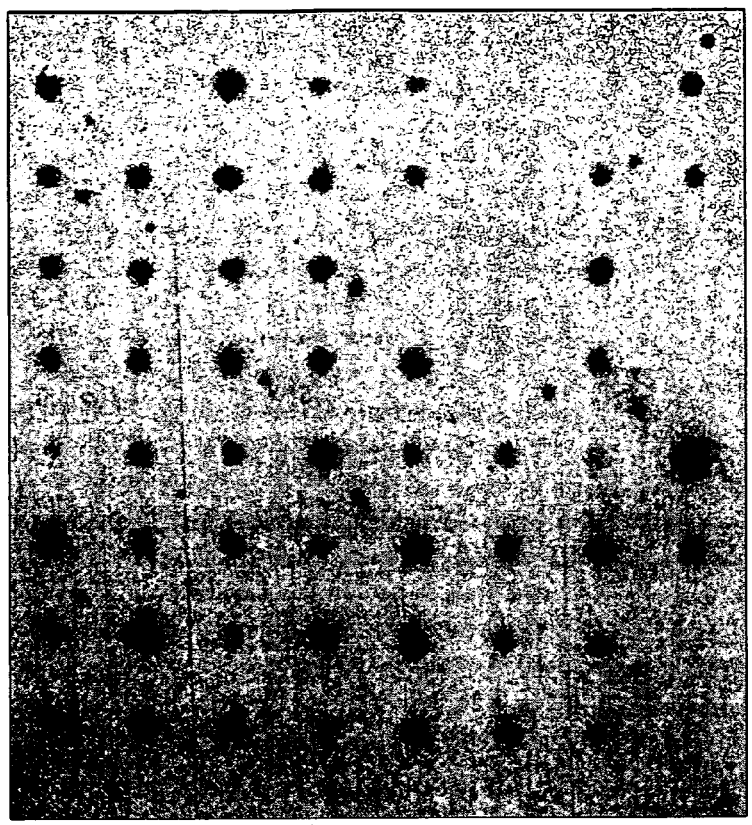

FIG. 3

HUMAN RNA MASTER BLOT PROBED WITH
$^{32}$P-LABELLED HUMAN PDE_XIV

| | 1 | 2 | 3 | 4 | 5 | 6 | 7 | 8 |
|---|---|---|---|---|---|---|---|---|
| A | WHOLE BRAIN | AMYG-DALA | CAUDATE NUCLEUS | CERE-BELLUM | CEREBAL CORTEX | FRONTAL LOBE | HIPPO-CAMPUS | MEDULLA OBLON-GATA |
| B | OCCIP-ITAL LOBE | PUTAMEN | SUBST-ANTIAL NIGRA | TEMP-ORAL LOBE | THALA-MUS | NUCLEUS ACCUM-BEUS | SPINAL CORD | |
| C | HEART | SORTA | SKELETAL MUSCLE | COLON | BLADDER | UTERUS | PROST-ATE | STOMACH |
| D | TESTIS | OVARY | PANC-REAS | PITUIT-ARY GLAND | ADRENAL GLAND | THYROID GLAND | SALIVARY GLAND | MAMM-ARY GLAND |
| E | KIDNEY | LIVER | SMALL INTE-STINE | SPLEEN | THYMUS | PERIPH-ERAL LEUKO-CYTE | LYMPH NODE | BONE MARROW |
| F | APPEN-DIX | LUNG | TRACHEA | PLACEN-TA | | | | |
| G | FETAL BRAIN | FETAL HEART | FETAL KIDNEY | FETAL LIVER | FETAL SPLEEN | FETAL THYMUS | FETAL LUNG | |
| H | YEAST TOTAL RNA 100ng | YEAST tRNA 100ng | E. COLI rRNA 100ng | E. COLI DNA 100ng | POLY r(A) 100ng | HUMAN C$_0$t1 DNA 100ng | HUMAN DNA 100ng | HUMAN DNA 500ng |

FIG. 4

Alignment of the Murine and Human PDE_XIV nucleotide sequence

New sequence is PDE_XIV

Pileup: Genetics Computer Group.
  MSF: 3134  Type: N   Check: 5422 ..

Name: mpdea_ oo  Len: 3134  Check: 5084  Weight: 0.001
Name: hspdea_ oo  Len: 3134  Check:  338  Weight: 0.100

```
new mpde_      1 AGGTACGCCT GCAGGTACCG GTCCGGAATT CCCGGGTCGA CCCACGCGTC
new hspde_       .......... .......... .......... .......... ..........

new mpde_     51 CGGCCAGCCT CCCAGGCCGG CTGCCTGCTC ACCCAGCCAG TCGCTAGCTC
new hspde_     1 .......... .......... .......... .......... .CGGAAT.TC mpdea_       101 TGGGCACTGC AGCAGGCTCG GCTCTGTCCC AGCGCTCGCT TGCTTGCTCG
hspde_         9 GATGCACTGC AGCAGGCTCG GCTCTGTCCC AGC....A.. ..........

mpdea_       151 CTCGCTCGGC TGGGAGAAAA GTGGTGTC.C TCGCCCAG.. AGAGCCTCTC
hspde_        43 ....CTTGTC TGGGAGAAAA GTGGTGTTAC TCACCCAGGG AGAGTCTCTC mpdea_       198 TCTC..CCTT CCTTCTTTCT CGAGCTCTCT GAGTCCTTTG GCGTTTCTTT
hspde_        89 TTTCTACCTT CCTTCTTTCT CGATCTCCTT GTGTGCTTTT GTGTTTCTTT mpdea_       246 CTTTCTTTCC TTTTTTTTTT TTTTTAATA  TTTTCTTTTT CTTTCTATAA
hspde_       139 ATTTCTTTTC CTTTTTTTC  TT........ TTTTTTTTTT GTTACT....

mpde_        296 AACTTGCATA ATTATACTGC TAATCCTGGA TGAGGTTGCT GGATTCTGCA
hspde_       177 ........TA ATTATATTCC TAATCCTGGA TGAAGTTGCT GGATTCTGCA mpde_        346 GCACAAATCT TCATGAACAA GCCGCACCGC TCAGAGATTT CACAGCATTC
hspde_       219 GCACAAGTCT TCATGAACAA GCAGCACCGC TCAGAGATTT CACGGCATTC
                                                     start codon
mpde_        396 AAAGGTCACA GAACTGCCAC TATGGTTAAA TGTCTTGTTT AATGGTTGAG
hspde_       269 AAAGGTCACA GAACTGCCAC TATGGTTAAA TGTCTTGTTT AATGGTTGAG mpdea_       446 AGGTGTGGCG AAGTCTTGTT TGAGAGCCCT GAACAGAGTG TCAAATGTGT
hspde_       319 AGGTGTGGCG AAATCTTGTT TGAGAACCCC GATCAGAATG CCAAATGTGT mpde_        496 TTGCATGCTA GGAGATGTAC GACTAAGGGG TCAGACGGGG GTTCCTGCCG
hspde_       369 TTGCATGCTG GGAGATATAC GACTAAGGGG TCAGACGGGG GTTCGTGCTG mpde_        546 AACGCCGTGG CTCCTACCCA TTCATTGACT TCCGTCTACT TAACAATACA
hspde_       419 AACGCCGTGG CTCCTACCCA TTCATTGACT TCCGCCTACT TAACAGTACA mpde_        596 ACACACTCAG GGGAAATTGG CACCAAGAAA AAGGTGAAAC GACTGTTAAG
hspde_       469 ACATACTCAG GGGAGATTGG CACCAAGAAA AAGGTGAAAA GACTATTAAG mpde_        646 TTTCCAAAGA TACTTCCATG CATCTAGGCT TCTCCGGGGG ATTATACCGC
hspde_       519 CTTTCAAAGA TACTTCCATG CATCAAGGCT GCTTCGTGGA ATTATACCAC mpde_        696 AGGCCCCTCT CCACCTGCTG GATGAAGACT ACCTTGGACA AGCAAGGCAC
hspde_       569 AAGCCCCTCT GCACCTGCTG GATGAAGACT ACCTTGGACA AGCAAGGCAT mpde_        746 ATGCTCTCCA AAGTTGGAAC GTGGGACTTT GACATTTTCT TGTTTGATCG
hspde_       619 ATGCTCTCCA AAGTGGGAAT GTGGGATTTT GACATTTTCT TGTTTGATCG
```

FIG. 4 CONT'D

```
mpde_    796  CTTGACAAAT GGGAACAGTC TGGTAACTCT GTTGTGTCAC CTCTTCAACT
hspde_   669  CTTGACAAAT GGAAACAGCC TGGTAACACT GTTGTGCCAC CTCTTCAATA mpde_    846  CCCATGGGCT CATCCACCAT TTCAAGCTCG ATATGGTGAC CTTGCACAGG
hspde_   719  CCCATGGACT CATTCACCAT TTCAAGTTAG ATATGGTGAC CTTACACCGA mpde_    896  TTTCTGGTTA TGGTTCAGGA AGATTACCAC GGTCACAACC CATACCACAA
hspde_   769  TTTTTAGTCA TGGTTCAAGA AGATTACCAC AGCCAAAACC CGTATCACAA mpde_    946  TGCTGTTCAC GCAGCCGACG TCACCCAGGC CATGCACTGT TACCTGAAGG
hspde_   819  TGCTGTTCAC GCAGCCGACG TCACCCAGGC CATGCACTGC TACCTGAAAG mpde_    996  AGCCAAAGTT GGCAAGCTTC CTCACACCTC TGGACATCAT GCTTGGACTA
hspde_   869  AGCCAAAGCT TGCCAGCTTC CTCACGCCTC TGGACATCAT GCTTGGACTG mpde_   1046  CTGGCTGCAG CAGCTCATGA CGTGGACCAC CCAGGGGTCA ACCAGCCATT
hspde_   919  CTGGCTGCAG CAGCACACGA TGTGGACCAC CCAGGGGTGA ACCAGCCATT mpde_   1096  TTTGATCAAA ACTAACCACC ATCTTGCCAA CCTGTATCAG AATATGTCTG
hspde_   969  TTTGATAAAA ACTAACCACC ATCTTGCAAA CCTATATCAG AATATGTCTG mpde_   1146  TACTGGAGAA TCACCACTGG CGATCTACAA TTGGCATGCT TCGAGAATCA
hspde_  1019  TGCTGGAGAA TCATCACTGG CGATCTACAA TTGGCATGCT TCGAGAATCA mpde_   1196  CGGCTCCTGG CTCACTTGCC AAAGGAAATG ACACAGG... .....ATATC
hspde_  1069  AGGCTTCTTG CTCATTTGCC AAAGGAAATG ACGTAAGTGC TGCCAGATG
                                                    stop codon mpde_   1238  GAACA..... ....GCA... ......GCTG GGCTCCCTCA TCTTGGCCAC
hspde_  1119  AAACATACTG ATGTGCATGC AGTAAAGATA AGCCACTTTC TCTAGGGCA.

mpde_   1270  GGATATCAAC AGACAGAATG AGTTTCTGA. ......CCCG CTTAAAAGCT
hspde_  1168  GGCTTGGGAC CTTTTGCGTG AATGGCAGAG AGCCCCCCGG CTGTACTTCC mpde_   1313  CACCTCCACA ATAAAGATT. TGAGAC.... ..TGGAGAAT GT.ACAGGA.
hspde_  1218  TGCCTGCACT GAGCTGTCTA TCAGAGGAGA TTTGGTGTCA GTTACAGCAA mpde_   1354  ..CAGACACT TTATGCT.TC AGATCGCCTT GAAGTGTGCT GACATTTGCA
hspde_  1268  CCCAGAAACC AAAATCTCTC TGTGTGCTTT GAAAGGGCCT TGCAGAGTCA mpde_   1401  AT..CCTT.. GTC.GTATCT GGGAGATGAG CAAGCAGT.. GGAGTGAAAG
hspde_  1318  ATGACCTACA GTCAGGAAAA GGGATAATAA ACAGCTCTCA GTTTTCACAC mpde_   1444  GGT....... CTGTGAGGAA TTCTACAGAC AAGGTGACCT TGAAC..AG.
hspde_  1368  GCTTCAGTAT CAGTGCTCAA CTTTGCCAAA TTCCCGACCT TTAGTTTAGC mpde_   1484  AAGTTTGAAC TGGAAATCAG .TCCTCTTTG TAATCAAC.A GAAAGATTCA
hspde_  1418  AAAATTGTCC TTCCATGTAG CTCCAAATAG TAAATATTTA TCAAGAAGGA mpde_   1532  ATCCCTAGCA TACAAA...T TGGTTTCATG ACT.TACATC GTGGAGCCGC
hspde_  1468  A.CCCAGGCA TTCTAAAGCT AGAGTTCAAA AAGTATATT TTGTAATTGC mpde_   1578  TGTTCCGGG. ...AGTGG.. GCCCGGTTTA CTGGG..AAC AGCACCCTGT
hspde_  1517  TAGTCTCAGC AAAAATAGAA GTCAGAAATT CTTTTCTAAA ATGTCTTTTG mpde_   1620  CGGAGAACAT GCTAAGCC.. ....ATCTCG CGCACAACAA AGCCCAGTGG
hspde_  1567  CTAAGTAATT GAAATGGCCC TAGCATTTTT TTCACCAATT AATTTACCTT mpde_   1664  AAGAGCCT.G CTGTCCAATC AGCAC...AG ACGCA..... ...GGGGCAG
hspde_  1617  ACGTCTCTTG CACTTTAAAC AGAAGGGGAG ACACTCATTT TCTGGTTCAC mpde_   1702  CG.......G CCAGGACCTG GCGG....GC CCCGC...AC CTGAGACCCT
hspde_  1667  TATTTGATAG CCATGGTATG TAGGCTGAGT CCCACTAAAT CTGAGGCCAT
```

FIG. 4CONT'D

```
                                                 stop codon
mpde_    1738  GGAG.CAGAC  AGAAGGTGCC  ACGCCCTAAG  GTAGCTGTC.  .TGCTGA..T
hspde_   1717  TGTTTCATTT  TCCTGGTG..  ..GCCCCAAG  TTAGCTGCTA  ATACTGTCTT mpde_    1783  GCACGGCCA.  .......TCT  G.TCCGTCCA  .....CAGGA  GCACGGCC...
hspde_   1763  CCAAGGCCAC  CATTAATTCT  GATCTGTTTA  ATGAACACGT  GCAGAACCCA mpde_    1817  ...ATCC...  .........G  TCC...GACT  GC........  .CCTCGCAAC
hspde_   1813  AGAAACCTAG  GTGAAAAGAG  TACATAGATT  GCTGTACCCT  TCTTCAAGAC mpde_    1840  AAGCCCATCA  CGCTGGGTTT  CGATGCCAT.  .CCGCCTGCC  A.CTTACC..
hspde_   1863  AAGCACATAA  CTTGAGGTCA  AGGACCAAGT  GCTGTCTCCC  AACTGAACAA mpde_    1885  ...GCCTCCC  TTCGTTGATC  CAAGTGTACA  AAAGCCATTG  ...TCACCTC
hspde_   1913  GCAGTATACT  CTGGGTTGTG  GATTGATTCC  TGGCCCTCTG  ATTTGATCTC mpde_    1929  AGCAT.....  .TAGCTGCC.  ...GAAATGGG  CGGCTCTATC  CCGTCATTGG
hspde_   1963  ATGCTGTTTC  CTAGCACCCA  GAGGAATGTG  AAATTTGCAG  GAGGAATTTC mpde_    1970  AG..CTGAT.  ....TCTGGGG  CGGCTGCCCC  AACCGAAAC.  .........G
hspde_   2013  AGTTCTGATA  AATTTTTACT  CCCTGGAACT  AAATAAAACC  AGTTCTCGTG mpde_    2004  CCTGGAAGTA  AGAA..AGGG  GTGCTTCTGC  CGTGTTCGCC  TCTGGCCCTT
hspde_   2063  CATGGAATAA  AAACTTATGC  CTCTTACTAG  AATAATAAAT  TGCAAAGATT mpde_    2052  GGTCACGCTG  ACTGGCAGTA  GCTCCTAAGT  CCAGAGCATT  TTAACGTTTG
hspde_   2113  GAAAGAATTA  AATGCAAAAA  GAACTAAAAA  CTAGAGCAAA  AGATCAAGTG mpde_    2102  CCATC..GGA  CAGCTGACCT  ...GCATGAC  ACCAGCAT..  .ACTTGGAAC
hspde_   2163  AGAAGAAGAA  AAGAGGAGGT  AAGGAGAGAG  ACAAGGAAGA  AAGAAGGAGA mpde_    2144  TGCAAAACTG  GTCTTGCGTG  CCAGAGCACA  AACGAGAGTG  TGAGAGAAA.
hspde_   2213  AGGAAAGGAA  GAATAGTGAG  G.ACAGGAAA  GAAGAAAATG  CAAGGGAAAT mpde_    2193  ..GTACCTTC  TATTT..TAA  TAATAATTAT  TATTATAAAA  TA....ATAA.
hspde_   2262  GGGAAAGGAC  TCTGGGGTGA  CCAGACTTCT  CCTGGTCAGT  ACCTGCATTC mpde_    2235  ATCTTTTTAA  CTTTT..ATA  TTTCATGCAC  CAGACAATGG  GTCTAAAACT
hspde_   2312  ATCCTGTTTG  TTACTCAATA  TTTCTTTCCT  AAAATATTCA  TTTCACATCT mpde_    2283  TTGGA...CA  AGTAATACTC  TGCGTACCCA  AACCTAAGAG  G......GGG
hspde_   2362  ATGGATTCCA  ATGAAAAATA  TATTTTTATG  TGTCTTTGTG  GAACACAGTG mpde_    2324  TTC...ATTA  TTTT.GCTAT  T.GACTC...  ..TATGCCAC  ATTGGGTCCG
hspde_   2412  TTATAAATTG  TTTTTGCCAG  AAGAATAATT  GTTATACAAT  AATATATGTG mpde_    2364  AGA..TGTGG  CACCATTGCG  ATTTCTGAAA  CCACGCGTCC  .CCTCCCATC
hspde_   2462  AAAACTTTAT  TACAAAAGCC  ATTATCATAA  TCATTATTAT  TCCTTCTATC mpde_    2411  TGGTGGAAGG  TGCTGTACAG  CCCGTCCC..  ..TTTGCACC  GTTAGCCAAT
hspde_   2512  ACA.GGTAAA  TGCTTTAATG  TCATTTTTCT  GATTTTAAAA  GTAGGGCAGG mpde_    2457  CCGTCTTT..  .....TACGGA  ...TTCAGTG  ACCTGTTTAT  ATTCACAA.G
hspde_   2561  TTAATTGTAG  AAAGTAAGGA  AAATTCAGGA  AAGTGTTAGT  TTGAACTATG mpde_    2497  TGTACATTTT  CTGT..AAAT  ACCAAACGCT  ACTGA.....  ......TTCC
hspde_   2611  TGAAGTTGCT  CTTTTTAAGG  GCCAAAAACA  GGAGACTTTT  AGCACTTTCA mpde_    2534  CATGC..CA.  ....AAATAC  ACGAGTATTA  TGGGATTGCT  A.....CCTG
hspde_   2661  TATGTTTCAG  CTTGATATGA  AAGAGAAAAC  TGAAACTGCT  AGTAATCCTG mpde_    2571  .........T  ATAAACAATG  GCACTGTGAA  CAGAATA...  .CTGTTAGTT
hspde    2711  CCATCCAGGT  ATAGTTCATG  TTAACCTGGC  TAGTTTATTT  TCTTTTAGTC
```

FIG. 4CONT'D

```
mpde_    2608  TTAATACAAG AGAATGCATT TGTAAATATG GTATAGAGTT TATTAATATA
hspde_   2761  TTTTTTCAAT ACAAA.CTTA TTTTAACAAA ATAT.GATTA TATTTGGGGA mpde_    2658  CTGTTGTTCG CAGATAAAGG CCTTAACTTT AAAAAAAAAA AAAAAAAA.
hspde_   2809  ACTTATTTTA CAGTTTACGT CCTGAAATTT TTTATTTACA ATAAAGACTT mpde_    2708  ......:AAAA AAAAAAAAAA AAAAAGGGGC GGCCGCTCTA GAGGATCCCT
hspde_   2859  TTTTCCAAAT CAAAAAAAAA.AAAAAAGGGC GGCCGCTCTA GAGGATCCCT mpde_    2752  CGAGGGGCCC AAGCTTACGC GTGCATGCGA CGTCATAGCT CTCTCCCTAT
hspde_   2909  CGAGGGGCCC AAGCTTACGC GTGCATGCGA CGTCATAGCT CTCTCCCTAT mpde_    2802  AGTGAGTCGT ATTATAAGCT AG........ .... 2823
hspde_   2959  AGTGAGTCGT ATTATAAGCT AGGCACTGGC CGTC 2992
```

FIG. 5

Protien Alignment of the Murine & Human PDE_XIV

CLUSTAL W (1.7) multiple sequence alignment

```
mpde     MSCLMVERCGEVLFESPEQSVKCVCMLGDVRLRGQTGVPAERRGSYPFIDFRLLNNTTHS  60
hspde    MSCLMVERCGEILFENPDQNAKCVCMLGDIRLRGQTGVRAERRGSYPFIDFRLLNSTTYS  60
         **********:*.*:*..*****:*** *********.:* mpde     GEIGTKKKVKRLLSFQRYFHASRLLRGIIPQAPLHLLDEDYLGQARHMLSKVGTWDFDIF  120
hspde    GEIGTKKKVKRLLSFQRYFHASRLLRGIIPQAPLHLLDEDYLGQARHMLSKVGMWDFDIF  120
         ************************************************** **** mpde     LFDRLTNGNSLVTLLCHLFNSHGLIHHFKLDMVTLHRFLVMVQEDYHGHNPYHNAVHAAD  180
hspde    LFDRLTNGNSLVTLLCHLFNTHGLIHHFKLDMVTLHRFLVMVQEDYHSQNPYHNAVHAAD  180
         ******************.*******************:. :********* mpde     VTQAMHCYLKEPKLASFLTPLDIMLGLLAAAAHDVDHPGVNQPFLIKTNHHLANLYQNMS  240
hspde    VTQAMHCYLKEPKLASFLTPLDIMLGLLAAAAHDVDHPGVNQPFLIKTNHHLANLYQNMS  240
         ************************************************************ mpde     VLENHHWRSTIGMLRESRLLAHLPKEMTQDIEQQLGSLILATDINRQNEFLTRLKAHLHN  300
hspde    VLENHHWRSTIGMLRESRLLAHLPKEMT--------------------------------  268
         *************************** mpde     KDLRLENVQDRHFMLQIALKCADICNPCRIWEMSKQWSERVCEEFYRQGDLEQKFELEIS  360
hspde    ------------------------------------------------------------ mpde     PLCNQQKDSIPSIQIGFMTYIVEPLFREWARFTGNSTLSENMLSHLAHNKAQWKSLLSNQ  420
hspde    ------------------------------------------------------------ mpde     HRRRGSGQDLAGPAPETLEQTEGATP  446
hspde    --------------------------
```

Zinc binding motif's are highlighted in bold.
Non-Catalytic domain in italics.

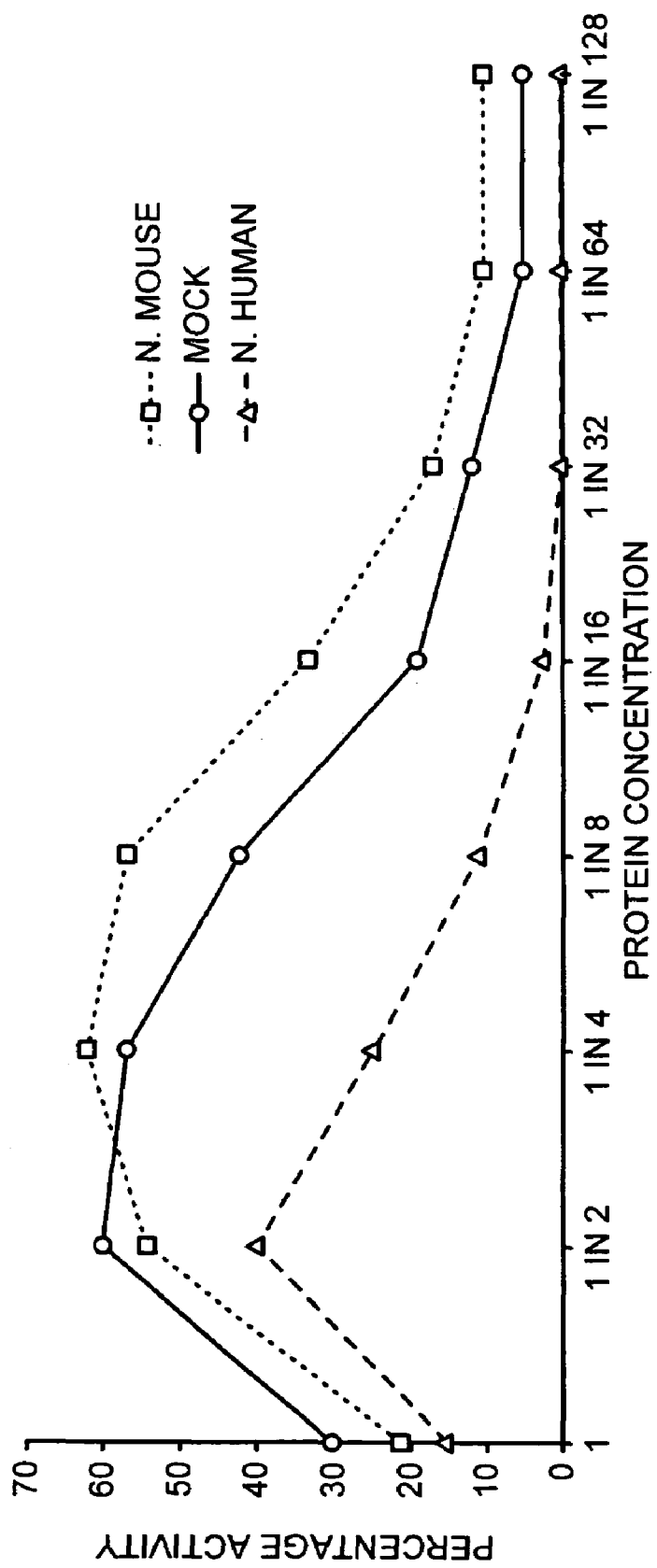

SEQUENCE LISTING

```
<160> NUMBER OF SEQ ID NOS: 26

<210> SEQ ID NO 1
<211> LENGTH: 446
<212> TYPE: PRT
<213> ORGANISM: Mouse

<400> SEQUENCE: 1

Met Ser Cys Leu Met Val Glu Arg Cys Gly Glu Val Leu Phe Glu Ser
1               5                   10                  15
```

```
Pro Glu Gln Ser Val Lys Cys Val Cys Met Leu Gly Asp Val Arg Leu
            20                  25                  30

Arg Gly Gln Thr Gly Val Pro Ala Glu Arg Arg Gly Ser Tyr Pro Phe
            35                  40                  45

Ile Asp Phe Arg Leu Leu Asn Asn Thr Thr His Ser Gly Glu Ile Gly
 50                      55                  60

Thr Lys Lys Lys Val Lys Arg Leu Leu Ser Phe Gln Arg Tyr Phe His
65                   70                  75                   80

Ala Ser Arg Leu Leu Arg Gly Ile Ile Pro Gln Ala Pro Leu His Leu
                 85                  90                  95

Leu Asp Glu Asp Tyr Leu Gly Gln Ala Arg His Met Leu Ser Lys Val
            100                 105                 110

Gly Thr Trp Asp Phe Asp Ile Phe Leu Phe Asp Arg Leu Thr Asn Gly
            115                 120                 125

Asn Ser Leu Val Thr Leu Leu Cys His Leu Phe Asn Ser His Gly Leu
130                     135                 140

Ile His His Phe Lys Leu Asp Met Val Thr Leu His Arg Phe Leu Val
145                 150                 155                 160

Met Val Gln Glu Asp Tyr His Gly His Asn Pro Tyr His Asn Ala Val
                165                 170                 175

His Ala Ala Asp Val Thr Gln Ala Met His Cys Tyr Leu Lys Glu Pro
            180                 185                 190

Lys Leu Ala Ser Phe Leu Thr Pro Leu Asp Ile Met Leu Gly Leu Leu
            195                 200                 205

Ala Ala Ala Ala His Asp Val Asp His Pro Gly Val Asn Gln Pro Phe
210                     215                 220

Leu Ile Lys Thr Asn His His Leu Ala Asn Leu Tyr Gln Asn Met Ser
225                 230                 235                 240

Val Leu Glu Asn His His Trp Arg Ser Thr Ile Gly Met Leu Arg Glu
                245                 250                 255

Ser Arg Leu Leu Ala His Leu Pro Lys Glu Met Thr Gln Asp Ile Glu
            260                 265                 270

Gln Gln Leu Gly Ser Leu Ile Leu Ala Thr Asp Ile Asn Arg Gln Asn
            275                 280                 285

Glu Phe Leu Thr Arg Leu Lys Ala His Leu His Asn Lys Asp Leu Arg
290                 295                 300

Leu Glu Asn Val Gln Asp Arg His Phe Met Leu Gln Ile Ala Leu Lys
305                 310                 315                 320

Cys Ala Asp Ile Cys Asn Pro Cys Arg Ile Trp Glu Met Ser Lys Gln
                325                 330                 335

Trp Ser Glu Arg Val Cys Glu Glu Phe Tyr Arg Gln Gly Asp Leu Glu
            340                 345                 350

Gln Lys Phe Glu Leu Glu Ile Ser Pro Leu Cys Asn Gln Gln Lys Asp
            355                 360                 365

Ser Ile Pro Ser Ile Gln Ile Gly Phe Met Thr Tyr Ile Val Glu Pro
370                 375                 380

Leu Phe Arg Glu Trp Ala Arg Phe Thr Gly Asn Ser Thr Leu Ser Glu
385                 390                 395                 400

Asn Met Leu Ser His Leu Ala His Asn Lys Ala Gln Trp Lys Ser Leu
                405                 410                 415

Leu Ser Asn Gln His Arg Arg Gly Ser Gly Gln Asp Leu Ala Gly
            420                 425                 430

Pro Ala Pro Glu Thr Leu Glu Gln Thr Glu Gly Ala Thr Pro
```

-continued

```
                435              440              445
```

<210> SEQ ID NO 2
<211> LENGTH: 1341
<212> TYPE: DNA
<213> ORGANISM: Mouse

<400> SEQUENCE: 2

| | | | | | |
|---|---|---|---|---|---|
| atgtcttgtt | taatggttga | gaggtgtggc | gaagtcttgt | ttgagagccc | tgaacagagt | 60 |
| gtcaaatgtg | tttgcatgct | aggagatgta | cgactaaggg | gtcagacggg | ggttcctgcc | 120 |
| gaacgccgtg | gctcctaccc | attcattgac | ttccgtctac | ttaacaatac | aacacactca | 180 |
| ggggaaattg | gcaccaagaa | aaaggtgaaa | cgactgttaa | gtttccaaag | atacttccat | 240 |
| gcatctaggc | ttctccgggg | gattataccg | caggcccctc | tccacctgct | ggatgaagac | 300 |
| taccttggac | aagcaaggca | catgctctcc | aaagttggaa | cgtgggactt | tgacattttc | 360 |
| ttgtttgatc | gcttgacaaa | tgggaacagt | ctggtaactc | tgttgtgtca | cctcttcaac | 420 |
| tcccatgggc | tcatccacca | tttcaagctc | gatatggtga | ccttgcacag | gtttctggtt | 480 |
| atggttcagg | aagattacca | cggtcacaac | ccataccaca | atgctgttca | cgcagccgac | 540 |
| gtcacccagg | ccatgcactg | ttacctgaag | gagccaaagt | tggcaagctt | cctcacacct | 600 |
| ctggacatca | tgcttggact | actggctgca | gcagctcatg | acgtggacca | cccagggcgtc | 660 |
| aaccagccat | ttttgatcaa | aactaaccac | catcttgcca | acctgtatca | gaatatgtct | 720 |
| gtactggaga | tcaccactg | gcgatctaca | attggcatgc | ttcgagaatc | acggctcctg | 780 |
| gctcacttgc | caaaggaaat | gacacaggat | atcgaacagc | agctgggctc | cctcatcttg | 840 |
| gccacggata | tcaacagaca | gaatgagttt | ctgacccgct | aaaagctca | cctccacaat | 900 |
| aaagatttga | gactggagaa | tgtacaggac | agacactta | tgcttcagat | cgccttgaag | 960 |
| tgtgctgaca | tttgcaatcc | ttgtcgtatc | tgggagatga | gcaagcagtg | gagtgaaagg | 1020 |
| gtctgtgagg | aattctacag | acaaggtgac | cttgaacaga | agtttgaact | ggaaatcagt | 1080 |
| cctctttgta | atcaacagaa | agattcaatc | cctagcatac | aaattggttt | catgacttac | 1140 |
| atcgtggagc | cgctgttccg | ggagtgggcc | cggtttactg | ggaacagcac | cctgtcggag | 1200 |
| aacatgctaa | gccatctcgc | gcacaacaaa | gcccagtgga | agagcctgct | gtccaatcag | 1260 |
| cacagacgca | ggggcagcgg | ccaggacctg | gcgggccccg | cacctgagac | cctggagcag | 1320 |
| acagaaggtg | ccacgcccta | a | | | | 1341 |

<210> SEQ ID NO 3
<211> LENGTH: 288
<212> TYPE: PRT
<213> ORGANISM: Human

<400> SEQUENCE: 3

Met Ser Cys Leu Met Val Glu Arg Cys Gly Glu Ile Leu Phe Glu Asn
1               5                   10                  15

Pro Asp Gln Asn Ala Lys Cys Val Cys Met Leu Gly Asp Ile Arg Leu
            20                  25                  30

Arg Gly Gln Thr Gly Val Arg Ala Glu Arg Arg Gly Ser Tyr Pro Phe
        35                  40                  45

Ile Asp Phe Arg Leu Leu Asn Ser Thr Thr Tyr Ser Gly Glu Ile Gly
    50                  55                  60

Thr Lys Lys Val Lys Arg Leu Leu Ser Phe Gln Arg Tyr Phe His
65                  70                  75                  80

```
Ala Ser Arg Leu Leu Arg Gly Ile Ile Pro Gln Ala Pro Leu His Leu
                85                  90                  95
Leu Asp Glu Asp Tyr Leu Gly Gln Ala Arg His Met Leu Ser Lys Val
            100                 105                 110
Gly Met Trp Asp Phe Asp Ile Phe Leu Phe Asp Arg Leu Thr Asn Gly
        115                 120                 125
Asn Ser Leu Val Thr Leu Leu Cys His Leu Phe Asn Thr His Gly Leu
    130                 135                 140
Ile His His Phe Lys Leu Asp Met Val Thr Leu His Arg Phe Leu Val
145                 150                 155                 160
Met Val Gln Glu Asp Tyr His Ser Gln Asn Pro Tyr His Asn Ala Val
                165                 170                 175
His Ala Ala Asp Val Thr Gln Ala Met His Cys Tyr Leu Lys Glu Pro
            180                 185                 190
Lys Leu Ala Ser Phe Leu Thr Pro Leu Asp Ile Met Leu Gly Leu Leu
        195                 200                 205
Ala Ala Ala Ala His Asp Val Asp His Pro Gly Val Asn Gln Pro Phe
    210                 215                 220
Leu Ile Lys Thr Asn His His Leu Ala Asn Leu Tyr Gln Asn Met Ser
225                 230                 235                 240
Val Leu Glu Asn His His Trp Arg Ser Thr Ile Gly Met Leu Arg Glu
                245                 250                 255
Ser Arg Leu Leu Ala His Leu Pro Lys Glu Met Thr Gly Thr Trp Asp
            260                 265                 270
Phe Asp Ile Phe Leu Phe Asp Arg Leu Thr Asn Gly Asn Ser Leu Val
        275                 280                 285

<210> SEQ ID NO 4
<211> LENGTH: 807
<212> TYPE: DNA
<213> ORGANISM: Human

<400> SEQUENCE: 4
atgtcttgtt taatggttga gaggtgtggc gaaatcttgt ttgagaaccc cgatcagaat      60
gccaaatgtg tttgcatgct gggagatata cgactaaggg gtcagacggg ggttcgtgct     120
gaacgccgtg gctcctaccc attcattgac ttccgcctac ttaacagtac aacatactca     180
ggggagattg gcaccaagaa aaaggtgaaa agactattaa gctttcaaag atacttccat     240
gcatcaaggc tgcttcgtgg aattatacca caagcccctc tgcacctgct ggatgaagac     300
taccttggac aagcaaggca tatgctctcc aaagtgggaa tgtgggattt tgacattttc     360
ttgtttgatc gcttgacaaa tggaaacagc ctggtaacac tgttgtgcca cctcttcaat     420
acccatggac tcattcacca tttcaagtta gatatggtga ccttacaccg attttagtc     480
atggttcaag aagattacca cagccaaaac ccgtatcaca atgctgttca cgcagccgac     540
gtcacccagg ccatgcactg ctacctgaaa gagccaaagc ttgccagctt cctcacgcct     600
ctggacatca tgcttggact gctggctgca gcagcacacg atgtggacca cccaggggtg     660
aaccagccat ttttgataaa aactaaccac catcttgcaa acctatatca gaatatgtct     720
gtgctggaga atcatcactg gcgatctaca attggcatgc ttcgagaatc aaggcttctt     780
gctcatttgc caaaggaaat gacgtaa                                          807

<210> SEQ ID NO 5
<211> LENGTH: 450
<212> TYPE: PRT
```

<213> ORGANISM: Human

<400> SEQUENCE: 5

```
Met Ser Cys Leu Met Val Glu Arg Cys Gly Glu Ile Leu Phe Glu Asn
1               5                   10                  15

Pro Asp Gln Asn Ala Lys Cys Val Cys Met Leu Gly Asp Ile Arg Leu
            20                  25                  30

Arg Gly Gln Thr Gly Val Arg Ala Glu Arg Gly Ser Tyr Pro Phe
        35                  40                  45

Ile Asp Phe Arg Leu Leu Asn Ser Thr Thr Tyr Ser Gly Glu Ile Gly
50                  55                  60

Thr Lys Lys Val Lys Arg Leu Leu Ser Phe Gln Arg Tyr Phe His
65                  70                  75                  80

Ala Ser Arg Leu Leu Arg Gly Ile Ile Pro Gln Ala Pro Leu His Leu
                85                  90                  95

Leu Asp Glu Asp Tyr Leu Gly Gln Ala Arg His Met Leu Ser Lys Val
            100                 105                 110

Gly Met Trp Asp Phe Asp Ile Phe Leu Phe Asp Arg Leu Thr Asn Gly
        115                 120                 125

Asn Ser Leu Val Thr Leu Leu Cys His Leu Phe Asn Thr His Gly Leu
130                 135                 140

Ile His His Phe Lys Leu Asp Met Val Thr Leu His Arg Phe Leu Val
145                 150                 155                 160

Met Val Gln Glu Asp Tyr His Ser Gln Asn Pro Tyr His Asn Ala Val
                165                 170                 175

His Ala Ala Asp Val Thr Gln Ala Met His Cys Tyr Leu Lys Glu Pro
            180                 185                 190

Lys Leu Ala Ser Phe Leu Thr Pro Leu Asp Ile Met Leu Gly Leu Leu
        195                 200                 205

Ala Ala Ala Ala His Asp Val Asp His Pro Gly Val Asn Gln Pro Phe
210                 215                 220

Leu Ile Lys Thr Asn His His Leu Ala Asn Leu Tyr Gln Asn Met Ser
225                 230                 235                 240

Val Leu Glu Asn His His Trp Arg Ser Thr Ile Gly Met Leu Arg Glu
                245                 250                 255

Ser Arg Leu Leu Ala His Leu Pro Lys Glu Met Thr Gln Asp Ile Glu
            260                 265                 270

Gln Gln Leu Gly Ser Leu Ile Leu Ala Thr Asp Ile Asn Arg Gln Asn
        275                 280                 285

Glu Phe Leu Thr Arg Leu Lys Ala His Leu His Asn Lys Asp Leu Arg
290                 295                 300

Leu Glu Asp Ala Gln Asp Arg His Phe Met Leu Gln Ile Ala Leu Lys
305                 310                 315                 320

Cys Ala Asp Ile Cys Asn Pro Cys Arg Ile Trp Glu Met Ser Lys Gln
                325                 330                 335

Trp Ser Glu Arg Val Cys Glu Glu Phe Tyr Arg Gln Gly Glu Leu Glu
            340                 345                 350

Gln Lys Phe Glu Leu Glu Ile Ser Pro Leu Cys Asn Gln Gln Lys Asp
        355                 360                 365

Ser Ile Pro Ser Ile Gln Ile Gly Phe Met Ser Tyr Ile Val Glu Pro
370                 375                 380

Leu Phe Arg Glu Trp Ala His Phe Thr Gly Asn Ser Thr Leu Ser Glu
385                 390                 395                 400
```

```
Asn Met Leu Gly His Leu Ala His Asn Lys Ala Gln Trp Lys Ser Leu
                405                 410                 415
Leu Pro Arg Gln His Arg Ser Arg Gly Ser Ser Gly Ser Gly Pro Asp
            420                 425                 430
His Asp His Ala Gly Gln Gly Thr Glu Ser Glu Glu Gln Glu Gly Asp
        435                 440                 445
Ser Pro
    450
```

<210> SEQ ID NO 6
<211> LENGTH: 1353
<212> TYPE: DNA
<213> ORGANISM: Human

<400> SEQUENCE: 6

| | | | | | | |
|---|---|---|---|---|---|---|
| atgtcttgtt | taatggttga | gaggtgtggc | gaaatcttgt | ttgagaaccc | cgatcagaat | 60 |
| gccaaatgtg | tttgcatgct | gggagatata | cgactaaggg | gtcagacggg | ggttcgtgct | 120 |
| gaacgccgtg | gctcctaccc | attcattgac | ttccgcctac | ttaacagtac | aacatactca | 180 |
| ggggagattg | gcaccaagaa | aaaggtgaaa | agactattaa | gctttcaaag | atacttccat | 240 |
| gcatcaaggc | tgcttcgtgg | aattatacca | caagcccctc | tgcacctgct | ggatgaagac | 300 |
| taccttggac | aagcaaggca | tatgctctcc | aaagtgggaa | tgtgggattt | tgacattttc | 360 |
| ttgtttgatc | gcttgacaaa | tggaaacagc | ctggtaacac | tgttgtgcca | cctcttcaat | 420 |
| acccatggac | tcattcacca | tttcaagtta | gatatggtga | ccttacaccg | atttttagtc | 480 |
| atggttcaag | aagattacca | cagccaaaac | ccgtatcaca | atgctgttca | cgcagccgac | 540 |
| gtcacccagg | ccatgcactg | ctacctgaaa | gagccaaagc | ttgccagctt | cctcacgcct | 600 |
| ctggacatca | tgcttggact | gctggctgca | gcagcacacg | atgtggacca | cccaggggtg | 660 |
| aaccagccat | ttttgataaa | aactaaccac | catcttgcaa | acctatatca | gaatatgtct | 720 |
| gtgctggaga | tcatcactg | gcgatctaca | attggcatgc | ttcgagaatc | aaggcttctt | 780 |
| gctcatttgc | caaaggaaat | gacacaggat | attgaacagc | agctgggctc | cttgatcttg | 840 |
| gcaacagaca | tcaacaggca | gaatgaattt | ttgaccagat | tgaaagctca | cctccacaat | 900 |
| aaagacttaa | gactgaggga | tgcacaggac | aggcactttta | tgcttcagat | cgccttgaag | 960 |
| tgtgctgaca | tttgcaatcc | ttgtagaatc | tgggagatga | gcaagcagtg | gagtgaaagg | 1020 |
| gtctgtgaag | aattctacag | gcaaggtgaa | cttgaacaga | aatttgaact | ggaaatcagt | 1080 |
| cctctttgta | atcaacagaa | agattccatc | cctagtatac | aaattggttt | catgagctac | 1140 |
| atcgtggagc | cgctcttccg | ggaatgggcc | catttcacgg | gtaacagcac | cctgtcggag | 1200 |
| aacatgctgg | gccacctcgc | acacaacaag | gcccagtgga | agagcctgtt | gcccaggcag | 1260 |
| cacagaagca | ggggcagcag | tggcagcggg | cctgaccacg | accacgcagg | ccaagggact | 1320 |
| gagagcgagg | agcaggaagg | cgacagcccc | tag | | | 1353 |

<210> SEQ ID NO 7
<211> LENGTH: 2823
<212> TYPE: DNA
<213> ORGANISM: Mouse

<400> SEQUENCE: 7

| | | | | | | |
|---|---|---|---|---|---|---|
| aggtacgcct | gcaggtaccg | gtccggaatt | cccgggtcga | cccacgcgtc | cggccagcct | 60 |
| cccaggccgg | ctgcctgctc | acccagccag | tcgctagctc | tgggcactgc | agcaggctcg | 120 |
| gctctgtccc | agcgctcgct | tgcttgctcg | ctcgctcggc | tgggagaaaa | gtggtgtcct | 180 |

-continued

```
cgcccagaga gcctctctct cccttccttc tttctcgagc tctctgagtc ctttggcgtt    240
tctttctttc tttccttttt tttttttttt taatattttc tttttctttc tataaaactt    300
gcataattat actgctaatc ctggatgagg ttgctggatt ctgcagcaca aatcttcatg    360
aacaagccgc accgctcaga gatttcacag cattcaaagg tcacagaact gccactatgg    420
ttaaatgtct tgtttaatgg ttgagaggtg tggcgaagtc ttgtttgaga gccctgaaca    480
gagtgtcaaa tgtgtttgca tgctaggaga tgtacgacta aggggtcaga cgggggttcc    540
tgccgaacgc cgtggctcct acccattcat tgacttccgt ctacttaaca atacaacaca    600
ctcaggggaa attggcacca agaaaaaggt gaaacgactg ttaagtttcc aaagatactt    660
ccatgcatct aggcttctcc gggggattat accgcaggcc cctctccacc tgctggatga    720
agactacctt ggacaagcaa ggcacatgct ctccaaagtt ggaacgtggg actttgacat    780
tttcttgttt gatcgcttga caaatgggaa cagtctggta actctgttgt gtcacctctt    840
caactcccat gggctcatcc accatttcaa gctcgatatg gtgaccttgc acaggtttct    900
ggttatggtt caggaagatt accacggtca caacccatac cacaatgctg ttcacgcagc    960
cgacgtcacc caggccatgc actgttacct gaaggagcca agttggcaa gcttcctcac    1020 acctctggac atcatgcttg gactactggc tgcagcagct catgacgtgg accacccagg    1080
ggtcaaccag ccatttttga tcaaaactaa ccaccatctt gccaacctgt atcagaatat    1140
gtctgtactg gagaatcacc actggcgatc tacaattggc atgcttcgag aatcacggct    1200
cctggctcac ttgccaaagg aaatgacaca ggatatcgaa cagcagctgg gctccctcat    1260
cttggccacg gatatcaaca gacagaatga gtttctgacc cgcttaaaag ctcacctcca    1320
caataaagat ttgagactgg agaatgtaca ggacagacac tttatgcttc agatcgcctt    1380
gaagtgtgct gacatttgca atccttgtcg tatctgggag atgagcaagc agtggagtga    1440
aagggtctgt gaggaattct acagacaagg tgaccttgaa cagaagtttg aactggaaat    1500
cagtcctctt tgtaatcaac agaaagattc aatccctagc atacaaattg gtttcatgac    1560
ttacatcgtg gagccgctgt tccgggagtg ggcccggttt actgggaaca gcaccctgtc    1620
ggagaacatg ctaagccatc tcgcgcacaa caaagcccag tggaagagcc tgctgtccaa    1680
tcagcacaga cgcaggggca gcggccagga cctggcgggc cccgcacctg agaccctgga    1740
gcagacagaa ggtgccacgc cctaaggtag ctgtctgctg atgcacggcc atctgtccgt    1800
ccacaggagc acgccatcc gtccgactgc cctcgcaaca agcccatcac gctgggtttc    1860
gatgccatcc gcctgccact taccgcctcc cttcgttgat ccaagtgtac aaaagccatt    1920
gtcacctcag cattagctgc cgaaatgggc ggctctatcc cgtcattgga gctgattctg    1980
gggcggctgc cccaaccgaa acgcctggaa gtaagaaagg ggtgcttctg ccgtgttcgc    2040 ctctggcccct tggtcacgct gactggcagt agctcctaag tccagagcat tttaacgttt    2100
gccatcggac agctgacctg catgacacca gcatacttgg aactgcaaaa ctggtcttgc    2160
gtgccagagc acaaacgaga gtgtgagaga aagtaccttc tattttaata ataattatta    2220
ttataaaata ataaatcttt ttaactttta tatttcatgc accagacaat gggtctaaaa    2280
ctttggacaa gtaatactct gcgtacccaa acctaagagg gggttcatta ttttgctatt    2340
gactctatgc cacattgggt ccgagatgtg gcaccattgc gatttctgaa accacgcgtc    2400
ccctcccatc tggtggaagg tgctgtacag cccgtccctt tgcaccgtta gccaatccgt    2460
cttttacgga ttcagtgacc tgtttatatt cacaagtgta cattttctgt aaataccaaa    2520
```

```
cgctactgat tcccatgcca aaatacacga gtattatggg attgctacct gtataaacaa    2580
tggcactgtg aacagaatac tgttagtttt aatacaagag aatgcatttg taaatatggt    2640
atagagttta ttaatatact gttgttcgca gataaaggcc ttaactttaa aaaaaaaaa     2700 aaaaaaaaa aaaaaaaaa aaaaagggg cggccgctct agaggatccc tcgagggcc        2760 caagcttacg cgtgcatgcg acgtcatagc tctctcccta tagtgagtcg tattataagc    2820
tag                                                                   2823

<210> SEQ ID NO 8
<211> LENGTH: 2992
<212> TYPE: DNA
<213> ORGANISM: Human

<400> SEQUENCE: 8
cggaattcga tgcactgcag caggctcggc tctgtcccag cacttgtctg ggagaaaagt      60
ggtgttactc acccagggag agtctctctt tctaccttcc ttctttctcg atctccttgt     120
gtgcttttgt gtttctttat ttcttttcct tttttttctt ttttttttt gttacttaat     180 tatattccta atcctggatg aagttgctgg attctgcagc acaagtcttc atgaacaagc     240
agcaccgctc agagatttca cggcattcaa aggtcacaga actgccacta tggttaaatg     300
tcttgtttaa tggttgagag gtgtggcgaa atcttgtttg agaaccccga tcagaatgcc     360
aaatgtgttt gcatgctggg agatatacga ctaaggggtc agacgggggt tcgtgctgaa     420
cgccgtggct cctacccatt cattgacttc cgcctactta acagtacaac atactcaggg     480
gagattggca ccaagaaaaa ggtgaaaaga ctattaagct ttcaaagata cttccatgca     540
tcaaggctgc ttcgtggaat tataccacaa gcccctctgc acctgctgga tgaagactac     600
cttggacaag caaggcatat gctctccaaa gtgggaatgt gggattttga cattttcttg     660
tttgatcgct tgacaaatgg aaacagcctg gtaacactgt tgtgccacct cttcaatacc     720
catggactca ttcaccattt caagttagat atggtgacct acaccgattt tttagtcatg     780
gttcaagaag attaccacag ccaaaacccg tatcacaatg ctgttcacgc agccgacgtc     840
acccaggcca tgcactgcta cctgaaagag ccaaagcttg ccagcttcct cacgcctctg     900
gacatcatgc ttggactgct ggctgcagca gcacacgatg tggaccaccc aggggtgaac     960
cagccatttt tgataaaaac taaccaccat cttgcaaacc tatatcagaa tatgtctgtg    1020
ctggagaatc atcactggcg atctacaatt ggcatgcttc gagaatcaag gcttcttgct    1080
catttgccaa aggaaatgac gtaagtgctg ccgagatgaa acatactgat gtgcatgcag    1140
taaagataag ccactttctc tagggcaggc ttgggacctt ttgcgtgaat ggcagagagc    1200
cccccggctg tacttcctgc ctgcactgag ctgtctatca gaggagattt ggtgtcagtt    1260
acagcaaccc agaaaccaaa atctctctgt gtgctttgaa agggccttgc agagtcaatg    1320
acctacagtc aggaaagggg ataataaaca gctctcagtt tcacacgct tcagtatcag     1380 tgctcaactt tgccaaattc ccgaccttta gtttagcaaa attgtccttc catgtagctc    1440
caaatagtaa atatttatca agaaggaacc caggcattct aaagctagag ttcaaaaaag    1500
tatattttgt aattgctagt ctcagcaaaa atagaagtca gaaattcttt tctaaaatgt    1560
cttttgctaa gtaattgaaa tggccctagc attttttca ccaattaatt taccttacgt     1620
ctcttgcact ttaaacagaa ggggagacac tcattttctg gttcactatt tgatagccat    1680
ggtatgtagg ctgagtccca ctaaatctga ggccattgtt tcattttcct ggtggcccca    1740
agttagctgc taatactgtc ttccaaggcc accattaatt ctgatctgtt taatgaacac    1800
```

```
gtgcagaacc caagaaacct aggtgaaaag agtacataga ttgctgtacc cttcttcaag    1860
acaagcacat aacttgaggt caaggaccaa gtgctgtctc ccaactgaac aagcagtata    1920 ctctggttg tggattgatt cctggccctc tgatttgatc tcatgctgtt tcctagcacc     1980
cagaggaatg tgaaatttgc aggaggaatt tcagttctga taaattttta ctccctggaa    2040
ctaaataaaa ccagttctcg tgcatggaat aaaaacttat gcctcttact agaataataa    2100
attgcaaaga ttgaaagaat taaatgcaaa aagaactaaa aactagagca aaagatcaag    2160
tgagaagaag aaaagaggag gtaaggagag agacaaggaa gaaagaagga gaaggaaagg    2220
aagaatagtg aggacaggaa agaagaaaat gcaagggaaa tgggaaagga ctctggggtg    2280
accagacttc tcctggtcag tacctgcatt catcctgttt gttactcaat atttcttttcc   2340 taaaatattc atttcacatc tatggattcc aatgaaaaat atattttat gtgtctttgt     2400 ggaacacagt gttataaatt gttttttgcca gaagaataat tgttatacaa taatatatgt   2460
gaaaacttta ttacaaaagc cattatcata atcattatta ttccttctat cacaggtaaa    2520
tgctttaatg tcattttctct gattttaaaa gtagggcagg ttaattgtag aaagtaagga   2580
aaattcagga aagtgttagt ttgaactatg tgaagttgct cttttttaagg gccaaaaaca   2640 ggagactttt agcactttca tatgtttcag cttgatatga aagagaaaac tgaaactgct    2700
agtaatcctg ccatccaggt atagttcatg ttaacctggc tagtttatttt tcttttagtc   2760 tttttttcaat acaaacttat tttaacaaaa tatgattata tttggggaac ttattttaca   2820
gtttacgtcc tgaaattttt tatttacaat aaagactttt ttccaaatca aaaaaaaaa    2880 aaaagggcgg ccgctctaga ggatccctcg aggggcccaa gcttacgcgt gcatgcgacg    2940
tcatagctct ctcctataga tgagtcgtat tataagctag gcactggccg tc            2992
```

<210> SEQ ID NO 9
<211> LENGTH: 11
<212> TYPE: PRT
<213> ORGANISM: Mammalian

<400> SEQUENCE: 9

Met Ser Cys Leu Met Val Glu Arg Cys Gly Glu
1               5                   10

<210> SEQ ID NO 10
<211> LENGTH: 8
<212> TYPE: PRT
<213> ORGANISM: Mammalian

<400> SEQUENCE: 10

Lys Cys Val Cys Met Leu Gly Asp
1               5

<210> SEQ ID NO 11
<211> LENGTH: 8
<212> TYPE: PRT
<213> ORGANISM: Mammalian

<400> SEQUENCE: 11

Arg Leu Arg Gly Gln Thr Gly Val
1               5

<210> SEQ ID NO 12
<211> LENGTH: 16
<212> TYPE: PRT
<213> ORGANISM: Mammalian

<400> SEQUENCE: 12

Ala Glu Arg Arg Gly Ser Tyr Pro Phe Ile Asp Phe Arg Leu Leu Asn
1               5                   10                  15

<210> SEQ ID NO 13
<211> LENGTH: 54
<212> TYPE: PRT
<213> ORGANISM: Mammalian

<400> SEQUENCE: 13

Ser Gly Glu Ile Gly Thr Lys Lys Val Lys Arg Leu Leu Ser Phe
1               5                   10                  15

Gln Arg Tyr Phe His Ala Ser Arg Leu Leu Arg Gly Ile Ile Pro Gln
            20                  25                  30

Ala Pro Leu His Leu Leu Asp Glu Asp Tyr Leu Gly Gln Ala Arg His
        35                  40                  45

Met Leu Ser Lys Val Gly
        50

<210> SEQ ID NO 14
<211> LENGTH: 26
<212> TYPE: PRT
<213> ORGANISM: Mammalian

<400> SEQUENCE: 14

Trp Asp Phe Asp Ile Phe Leu Phe Asp Arg Leu Thr Asn Gly Asn Ser
1               5                   10                  15

Leu Val Thr Leu Leu Cys His Leu Phe Asn
            20                  25

<210> SEQ ID NO 15
<211> LENGTH: 26
<212> TYPE: PRT
<213> ORGANISM: Mammalian

<400> SEQUENCE: 15

His Gly Leu Ile His His Phe Lys Leu Asp Met Val Thr Leu His Arg
1               5                   10                  15

Phe Leu Val Met Val Gln Glu Asp Tyr His
            20                  25

<210> SEQ ID NO 16
<211> LENGTH: 99
<212> TYPE: PRT
<213> ORGANISM: Mammalian

<400> SEQUENCE: 16

Asn Pro Tyr His Asn Ala Val His Ala Ala Asp Val Thr Gln Ala Met
1               5                   10                  15

His Cys Tyr Leu Lys Glu Pro Lys Leu Ala Ser Phe Leu Thr Pro Leu
            20                  25                  30

Asp Ile Met Leu Gly Leu Leu Ala Ala Ala His Asp Val Asp His
        35                  40                  45

Pro Gly Val Asn Gln Pro Phe Leu Ile Lys Thr Asn His His Leu Ala
    50                  55                  60

Asn Leu Tyr Gln Asn Met Ser Val Leu Glu Asn His His Trp Arg Ser
65              70                  75                  80

Thr Ile Gly Met Leu Arg Glu Ser Arg Leu Leu Ala His Leu Pro Lys
                85                  90                  95

Glu Met Thr

<210> SEQ ID NO 17
<211> LENGTH: 38
<212> TYPE: PRT
<213> ORGANISM: Mammalian

<400> SEQUENCE: 17

Gln Asp Ile Glu Gln Gln Leu Gly Ser Leu Ile Leu Ala Thr Asp Ile
1               5                   10                  15

Asn Arg Gln Asn Glu Phe Leu Thr Arg Leu Lys Ala His Leu His Asn
            20                  25                  30

Lys Asp Leu Arg Leu Glu
        35

<210> SEQ ID NO 18
<211> LENGTH: 41
<212> TYPE: PRT
<213> ORGANISM: Mammalian

<400> SEQUENCE: 18

Gln Asp Arg His Phe Met Leu Gln Ile Ala Leu Lys Cys Ala Asp Ile
1               5                   10                  15

Cys Asn Pro Cys Arg Ile Trp Glu Met Ser Lys Gln Trp Ser Glu Arg
            20                  25                  30

Val Cys Glu Glu Phe Tyr Arg Gln Gly
        35                  40

<210> SEQ ID NO 19
<211> LENGTH: 28
<212> TYPE: PRT
<213> ORGANISM: Mammalian

<400> SEQUENCE: 19

Leu Glu Gln Lys Phe Glu Leu Glu Ile Ser Pro Leu Cys Asn Gln Gln
1               5                   10                  15

Lys Asp Ser Ile Pro Ser Ile Gln Ile Gly Phe Met
            20                  25

<210> SEQ ID NO 20
<211> LENGTH: 11
<212> TYPE: PRT
<213> ORGANISM: Mammalian

<400> SEQUENCE: 20

Tyr Ile Val Glu Pro Leu Phe Arg Glu Trp Ala
1               5                   10

<210> SEQ ID NO 21
<211> LENGTH: 12
<212> TYPE: PRT
<213> ORGANISM: Mammalian

<400> SEQUENCE: 21

Phe Thr Gly Asn Ser Thr Leu Ser Glu Asn Met Leu
1               5                   10

<210> SEQ ID NO 22
<211> LENGTH: 13
<212> TYPE: PRT
<213> ORGANISM: Mammalian

```
<400> SEQUENCE: 22

His Leu Ala His Asn Lys Ala Gln Trp Lys Ser Leu Leu
1               5                   10

<210> SEQ ID NO 23
<211> LENGTH: 7
<212> TYPE: PRT
<213> ORGANISM: Mammalian

<400> SEQUENCE: 23

Ser Gly Ser Gly Pro Asp His
1               5

<210> SEQ ID NO 24
<211> LENGTH: 30
<212> TYPE: DNA
<213> ORGANISM: Oligo

<400> SEQUENCE: 24
ggtcacagaa ctgccactat ggttaaatgt                                    30

<210> SEQ ID NO 25
<211> LENGTH: 22
<212> TYPE: DNA
<213> ORGANISM: Oligo

<400> SEQUENCE: 25
accgctcaga gatttcacag ca                                            22

<210> SEQ ID NO 26
<211> LENGTH: 22
<212> TYPE: DNA
<213> ORGANISM: Oligo

<400> SEQUENCE: 26
cccgtctgac cccttagtcg ta                                            22
```

ENZYME PDE XVI

REFERENCE TO RELATED APPLICATIONS

This application is filed claiming priority from co-pending Great Britain Application No. 9828603.2, filed Dec. 23, 1998, and Great Britain Application No. 9922123.6, filed Sep. 17, 1999.

BACKGROUND OF THE PRESENT INVENTION

The present invention relates to an enzyme. The present invention also relates to a nucleotide sequence encoding same.

In particular, the present invention relates to novel nucleic acid sequences encoding novel phosphodiesterase enzymes.

The present invention also relates to the use of the novel nucleic acid and amino acid sequences in the diagnosis and treatment of disease.

The present invention also relates to the use of the novel nucleic acid and amino acid sequences to evaluate and/or to screen for agents that can modulate phosphodiesterase activity.

The present invention further relates to genetically engineered host cells that comprise or express the novel nucleic acid and amino acid sequences to evaluate and/or to screen for agents that can modulate phosphodiesterase activity.

BACKGROUND ART

Cyclic nucleotides, such as cAMP and cGMP, are important intracellular second messengers. Cyclic nucleotide phosphodiesterases—otherwise known as PDEs—are a family of enzymes that catalyse the degradation of cyclic nucleotides and, in doing so, are one of the cellular components that regulate the concentration of cyclic nucleotides.

In recent years, at least ten PDE enzymes, as well as many subtypes of these enzymes, have been defined based on substrate affinity and cofactor requirements (Beavo J A and Reifsnyder D H, Trends Pharmacol. Sci. 11:150 [1990]; Beavo J, In: Cyclic Nucleotide Phosphodiesterases: Structure, Regulation and Drug Action., Beavo J and Housley M D (Eds.). Wiley:Chichester, pp. 3–15 [1990]).

Examples of sub-families include: PDE1 (sometimes written as PDEI), $Ca^{2+}$/calmodulin dependent; PDE2 (sometimes written as PDEII), cGMP-stimulated; PDE3 (sometimes written as PDEIII), cGMP-inhibited cAMP-hydrolysing; PDE4 (sometimes written as PDEIV), cAMP-specific, rolipram sensitive; PDE5 (sometimes written as PDEV), cGMP-specific; PDE6 (sometimes written as PDEVI), photoreceptor cGMP-specific; PDE7 (sometimes written as PDEVII), cAMP-specific, rolipram insensitive; PDE8 (sometimes written as PDEVIII), cAMP-specific IBMX insensitive; PDE9 (sometimes written as PDEIX), cGMP-specific IBMX insensitive; PDE10 (sometimes written as PDEX) dual substrate, IBMX sensitive.

PDEs contain a conserved C-terminal catalytic domain of ~270 amino acids (Charbonneau et al 1986 PNAS 83(24): 9308–12) and an N-terminal domain involved in regulating catalytic activity by binding cofactors, and in specifying subcellular localisation (Juilfs et al (1999) Rev Physiol Biochem Pharmacol 135:67–104).

Each PDE family may contain two or more isoforms (i.e. there may be two or more PDE isoenzymes). By way of example, mammalian PDE IV, the homologue of the *Drosophila* Dunce gene (Chen C N et al., Proc. Nat. Acad. Sci. (USA) 83:9313 [1986]), is known to have four isoforms in the rat (Swinnen J V et al., Proc. Nat. Acad. Sci. (USA) 86:5325 [1989]). Human PDEs are also known to occur as isoforms and have splice variants. For example, the cloning of one human isoform of PDEIV from monocytes was reported in 1990 (Livi G P et al., Mol. Cell. Bio., 10:2678 [1990]). By way of further example, other workers have independently cloned three splice variants of PDEIV, which are now designated hPDEIV-B1, hPDEIV-B2, and hPDEIV-B3.

Teachings on cyclic nucleotide phosphodiesterases can also be found in U.S. Pat. No. 5,932,423 and U.S. Pat. No. 5,932,465.

Teachings on a further cyclic nucleotide phosphodiesterase—namely CN PCDE8—can be found in WO-A-97/35989. According to WO-A-97/35989, CN PCDE8 has two isozymes—which were designated CN PCDE8A and CN PCDE8B. The term "isozyme" is sometimes referred to in the art as "isoform".

According to WO-A-97/35989, many inhibitors of different PDEs have been identified and some have undergone clinical evaluation. For example, PDEIII inhibitors are being developed as antithrombotic agents, as antihypertensive agents and as cardiotonic agents useful in the treatment of congestive heart failure. Rolipram, a PDEIV inhibitor, has been used in the treatment of depression and other inhibitors of PDEIV are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al 1995 AIDS 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al, 1995 Nat Med 1:244–248) and may be effective in the treatment of tardive dyskinesia (Sasaki et al, 1995 Eur J Phamacol 282:71–76).

According to WO-A-97/35989, there are also non-specific PDE inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al 1995 Respir J 8:996–1000) where it is thought to act by inhibiting both CN PDE cAMP and cGMP hydrolysis (Banner et al 1995 Monaldi Arch Chest Dis 50:286–292). Pentoxifylline, also known to block TNF-alpha production, may inhibit HIV-1 replication (Angel et al supra). A list of CN PDE inhibitors is given in Beavo 1995 supra.

It has been suggested that selective inhibitors of PDEs, in addition to their isozymes and their subtypes, will lead to more effective therapy with fewer side effects. For example, see the teachings in the reviews of Wieshaar R E et al, (J. Med. Chem., 28:537 [1985]), Giembycz M A (Biochem. Pharm., 43:2041 [1992]) and Lowe J A and Cheng J B (Drugs of the Future, 17:799–807 [1992]).

Thus, for some applications it is desirable to have a selective inhibition of an individual type of PDE. Hence, the cloning and expression of a novel PDE would greatly aid the discovery of selective inhibitors.

SUMMARY ASPECTS OF THE PRESENT INVENTION

Aspects of the present invention are presented in the claims and in the following commentary.
In brief, some aspects of the present invention relate to:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of treatment based on said novel sequences.
7. Pharmaceutical compositions based on said novel sequences.

Other aspects concerning the amino acid sequence of the present invention and/or the nucleotide sequence of the present invention include: a construct comprising or capable of expressing the sequences of the present invention; a vector comprising or capable of expressing the sequences of the present invention; a plasmid comprising or capable of expressing the sequences of present invention; a tissue comprising or capable of expressing the sequences of the present invention; an organ comprising or capable of expressing the sequences of the present invention; a transformed host comprising or capable of expressing the sequences of the present invention; a transformed organism comprising or capable of expressing the sequences of the present invention. The present invention also encompasses methods of expressing the same, such as expression in a micro-organism; including methods for transferring same.

For ease of reference, aspects of the present invention are now discussed under appropriate section headings. However, the teachings under each section are not necessarily limited to each particular section.

In the following commentary references to "nucleotide sequence of the present invention" and "amino acid sequence of the present invention" refer respectively to any one or more of the nucleotide sequences presented or discussed herein and to any one or more of the amino acid sequences presented or discussed herein. Also, and as used herein, "amino acid sequence" refers to peptide or protein sequences and may refer to portions thereof. In addition, the term "amino acid sequence of the present invention" is synonymous with the phrase "polypeptide sequence of the present invention". Also, the term "nucleotide sequence of the present invention" is synonymous with the phrase "polynucleotide sequence of the present invention".

DETAILED ASPECTS OF THE PRESENT INVENTION

According to a first aspect of the present invention there is provided an amino acid sequence comprising the sequence presented as Formula I or a variant, homologue, fragment or derivative thereof; wherein the amino acid sequence is capable of displaying PDE activity.

Formula I is presented as follows:

Formula I

An amino acid sequence comprising any one or more of peptide sequences or amino acids Z1–Z26, any of which peptide sequence or amino acid Z1–Z26 may be separated from another of said peptide sequence or amino acid Z1–Z26 by a suitable peptide sequence or amino acid residue;

wherein:

| | | |
|---|---|---|
| Z1 = MSCLMVERCGE | | (SEQ ID NO:9) |
| Z2 = LFE | | |
| Z3 = P | | |
| Z4 = Q | | |
| Z5 = KCVCMLGD | | (SEQ ID NO:10) |
| Z6 = RLRGQTGV | | (SEQ ID NO:11) |
| Z7 = AERRGSYPFIDFRLLN | | (SEQ ID NO:12) |
| Z8 = TT | | |
| Z9 = SGEIGTKKKVKRLLSFQRYFHASRLLRGIIPQAPLHLLDEDYLGQARHMLSKVG | | (SEQ ID NO:13) |
| Z10 = WDFDIFLFDRLTNGNSLVTLLCHLFN | | (SEQ ID NO:14) |
| Z11 = HGLIHHFKLDMVTLHRFLVMVQEDYH | | (SEQ ID NO:15) |
| Z12 = NPYHNAVHAADVTQAMHCYLKEPKLASFLTPLDIMLGLLAAAAHDVDHPGVNQPF LIKTNHHLANLYQNMSVLENHHWRSTIGMLRESRLLAHLPKEMT | | (SEQ ID NO:16) |
| Z13 = QDIEQQLGSLILATDINRQNEFLTRLKAHLHNKDLRLE | | (SEQ ID NO:17) |
| Z14 = QDRHFMLQIALKCADICNPCRIWEMSKQWSERVCEEFYRQG | | (SEQ ID NO:18) |
| Z15 = LEQKFELEISPLCNQQKDSIPSIQIGFM | | (SEQ ID NO:19) |
| Z16 = YIVEPLFREWA | | (SEQ ID NO:20) |
| Z17 = FTGNSTLSENML | | (SEQ ID NO:21) |
| Z18 = HLAHNKAQWKSLL | | (SEQ ID NO:22) |

-continued

Z19 = QHR

Z20 = RGS

Z21 = D

Z22 = AG

Z23 = E

Z24 = EQ

Z25 = EG

Z26 = P and wherein the amino acid sequence is made up of more than 200 amino acid residues.

For convenience, we now present a Table indicating the codes used for the amino acids.

| AMINO ACID | THREE LETTER ABBREVIATION | ONE LETTER SYMBOL |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

Here, Formula I is a generic formula. Formula I has been constructed from sequence analysis of the specific novel sequences presented herein.

For convenience, the PDE of the present invention is sometimes referred to as PDE_XIV. We also sometimes refer to this enzyme as being PDEXIV. If the enzyme is obtainable from human we use the suffix or prefix HS (or HM) or hs (or hm). If the enzyme is obtainable from mouse we use the suffix or prefix MM (or Mm or mm).

The PDE of the present invention is capable of catalysing the degradation of cAMP.

For Formula I any one or more of the amino acids may be an analogue thereof.

The term "analogue" as used herein means a sequence having a sequence similar to that of Formula I but wherein non-detrimental (i.e. not detrimental to enzymatic activity) amino acid substitutions or deletions have been made.

Preferably, the PDE enzyme of the present invention has at least two divalent cation binding motifs within the C-terminal catalytic domain and/or a conserved cAMP dependent protein kinase phosphorylation motif.

Preferably, the PDE enzyme of the present invention has at least two divalent cation binding motifs within the C-terminal catalytic domain and a conserved cAMP dependent protein kinase phosphorylation motif.

Preferably, the amino acid sequence of Formula I comprises at least 5 of Z1 to Z26.

Preferably, the amino acid sequence of Formula I comprises at least 10 of Z1 to Z26.

Preferably, the amino acid sequence of Formula I comprises at least 15 of Z1 to Z26.

Preferably, the amino acid sequence of Formula I comprises at least 20 of Z1 to Z26.

Preferably, the amino acid sequence of Formula I comprises at least 25 of Z1 to Z26.

Preferably, the amino acid sequence of Formula I comprises at least each of Z1 to Z26.

Preferably the amino acid sequence is made up of more than about 230 amino acid residues.

Preferably the amino acid sequence is made up of more than about 250 amino acid residues.

Preferably the amino acid sequence is made up of more than about 260 amino acid residues.

Preferably the amino acid sequence is made up of at least 268 amino acid residues.

Preferably, the amino acid sequence of Formula I comprises at least one or more of Z7, Z9, Z10, Z11, Z12, Z13, Z14, Z15, Z16, Z17 and Z18 or analogues thereof.

Preferably, the amino acid sequence of Formula I comprises at least each of Z7, Z9, Z10, Z11, Z12, Z13, Z14, Z15, Z16, Z17 and Z18 or analogues thereof.

Preferably, the amino acid sequence of Formula I comprises at least each of Z1, Z5, Z6, Z7, Z9, Z10, Z11, Z12, Z13, Z14, Z15, Z16, Z17 and Z18 or analogues thereof.

A preferred example of an amino acid sequence comprising the sequence presented as Formula I is the amino acid sequence shown as Formula II or a variant, homologue, fragment or derivative thereof.

Formula II

Z1-X1-Z2-X2-Z3-X3-Z4-X4-Z5-X5-Z6-X6-Z7-X7-Z8-X8-Z9-X9-Z10-X10-Z11-X11-Z12-
Z13-X12-Z14-X13-Z15-X14-Z16-X15-Z17-X16-Z18-X17-Z19-X18-Z20-X19-Z21-X20-Z22-
X21-Z23-X22-Z24-X23-Z25-X24-Z26 wherein
each of Z1–Z26 is as defined above; and
each of X1–X24 is independently selected from an optional suitable peptide sequence or amino acid.

A more preferred example of an amino acid sequence comprising the sequence presented as Formula I is the amino acid sequence shown as Formula III or a variant, homologue, fragment or derivative thereof.

Formula III

Z1-X1-Z2-X2-Z3-X3-Z4-X4-Z5-X5-Z6-X6-Z7-X7-Z8-X8-Z9-X9-Z10-X10-Z11-X11-Z12-

Z13-X12-Z14-X13-Z15-X14-Z16-X15-Z17-X16-Z18-X17-Z19-X18-Z20-X19-Z21-X20-Z22-

X21-Z23-X22-Z24-X23-Z25-X24-Z26 wherein
each of Z1–Z26 is as defined above; and

X1 = V or I

X2 = S or N

X3 = E or D

X4 = a peptide comprising at least two or more of S, V, N or A

X5 = V or I

X6 = P or R

X7 = N or S

X8 = H or Y

X9 = T or M

X10 = S or T

X11 = a peptide comprising at least two or more of G, H, S, Q

X12 = a peptide comprising at least two or more of D, A, N, V

X13 = E or D

X14 = S or T

X15 = H or R

X16 = G or S

X17 = a peptide comprising at least two or more of P, R, S, N

X18 = S or R

X19 = a peptide comprising at least two or more of S, G, P, D, H, Q

X20 = H or L

X21 = a peptide comprising at least two or more of Q, G, T, P, A

X22 = a peptide comprising at least two or more of S, E, T, L

X23 = optional T

X24 = a peptide comprising at least two or more of D, S, A, T

A more preferred example of an amino acid sequence comprising the sequence presented as Formula I is the amino acid sequence shown as Formula IV or a variant, homologue, fragment or derivative thereof.

Formula IV

Z1-X1-Z2-X2-Z3-X3-Z4-X4-Z5-X5-Z6-X6-Z7-X7-Z8-X8-Z9-X9-Z10-X10-Z11-X11-Z12-

-continued

Z13-X12-Z14-X13-Z15-X14-Z16-X15-Z17-X16-Z18-X17-Z19-X18-Z20-X19-Z21-X20-Z22-

X21-Z23-X22-Z24-X23-Z25-X24-Z26 wherein
each of Z1–Z26 is as defined above; and

```
X1  = V or I
X2  = S or N
X3  = E or D
X4  = SV or NA
X5  = V or I
X6  = P or R
X7  = N or S
X8  = H or Y
X9  = T or M
X10 = S or T
X11 = GH or SQ
X12 = DA or NV
X13 = E or D
X14 = S or T
X15 = H or R
X16 = G or S
X17 = PR or SN
X18 = S or R
X19 = SGSGPDH or GQ      (SEQ ID NO:23)
X20 = H or L
X21 = QGT or PAP
X22 = SE or TL
X23 = optional T
X24 = DS or AT
```

An example of a variant of any one of the above Formulae is an amino acid sequence wherein the group . . . $HZ_{17}GZ_{18}PRZ_{19}$ . . . is substituted with . . . $RZ_{17}SZ_{18}SNZ_{19}$ . . . .

Preferred examples of an amino acid sequence according to the present invention which comprises the sequence presented as Formula I include the amino acids shown as: SEQ ID NO:1 or SEQ ID NO:3 or SEQ ID NO:5, or a variant, homologue, fragment or derivative of any thereof.

It is to be noted that references to any one or more of the Formulae also apply equally to any one or more of: SEQ ID NO:1 or SEQ ID NO:3 or SEQ ID NO:5.

Preferably references to any one more of the Formulae herein mean any one or more of: SEQ ID NO:1 or SEQ ID NO:3 or SEQ ID NO:5.

More preferably references to any one or more of the Formulae mean a reference to SEQ ID NO:3 or 5.

According to a second aspect of the present invention there is provided an amino acid sequence comprising the sequence presented as Formula I.

According to a third aspect of the present invention there is provided a nucleotide sequence encoding the amino acid sequence of the present invention.

According to a fourth aspect of the present invention there is provided a nucleotide sequence comprising the sequence presented as SEQ ID NO:2 or SEQ ID NO:4 or SEQ ID NO:6, or a variant, homologue, fragment or derivative of any thereof.

According to a fifth aspect of the present invention there is provided a nucleotide sequence comprising the sequence presented as SEQ ID NO:2 or SEQ ID NO:4 or SEQ ID NO:6.

According to a sixth aspect of the present invention there is provided a nucleotide sequence that is capable of hybridising to the nucleotide sequence according to the present invention, or a sequence that is complementary thereto.

According to a seventh aspect of the present invention there is provided a nucleotide sequence that is capable of hybridising to the nucleotide sequence according to the sixth aspect of the present invention, or a sequence that is complementary thereto.

According to an eighth aspect of the present invention there is provided a vector comprising the nucleotide sequence according to the present invention.

According to a ninth aspect of the present invention there is provided a host cell into which has been incorporated the nucleotide sequence according to the present invention.

According to a tenth aspect of the present invention there is provided an assay method for identifying an agent that can affect PDE_XIV activity or expression thereof, the assay method comprising contacting an agent with an amino acid according to the present invention or a nucleotide sequence according to the present invention; and measuring the activity or expression of PDE_XIV; wherein a difference between a) PDE activity or expression in the absence of the agent and b) PDE activity or expression in the presence of the agent is indicative that the agent can affect PDE_XIV activity or expression.

Preferably the assay is to screen for agents useful in the treatment of disorders found in any one or more of the putamen, the Caudate nucleus of the brain, the Occipital lobe of the brain, the heart, ovary, the pituitary gland, kidney, liver, small intestine, thymus, skeletal muscle, leukocyte regions, dorsal root ganglia, uterus, cochlea, small intestine (duodenum), astrocytoma, and appendix.

According to an eleventh aspect of the present invention there is provided a process comprising the steps of: (a) performing the assay according to the present invention; (b) identifying one or more agents that do affect PDE_XIV activity or expression; and (c) preparing a quantity of those one or more identified agents.

According to a twelfth aspect of the present invention there is provided a method of affecting in vivo PDE_XIV activity or expression with an agent; wherein the agent is capable of affecting PDE_XIV activity or expression in an in vitro assay method; wherein the in vitro assay method is the assay method of the present invention.

According to a thirteenth aspect of the present invention there is provided the use of an agent in the preparation of a pharmaceutical composition for the treatment of a disease or condition associated with PDE_XIV, the agent is capable of having an effect on the activity or expression of PDE when assayed in vitro by the assay method of the present invention.

According to a fourteenth aspect of the present invention there is provided an enzyme capable of having an immunological reaction with an antibody raised against PDE_XIV.

According to a fifteenth aspect of the present invention there is provided a nucleotide sequence coding for a PDE, wherein the nucleotide sequence is obtainable from NCIMB 40995 or NCIMB 40996 or NCIMB 41027.

According to a sixteenth aspect of the present invention there is provided a PDE wherein the PDE is expressable from a nucleotide sequence obtainable from NCIMB 40995 or NCIMB 40996 or NCIMB 41027.

According to a seventeenth aspect of the present invention there is provided the use of an agent which has an effect on the activity of PDE_XIV or the expression thereof in the preparation of a pharmaceutical composition for the treatment of a disease or condition associated with PDE_XIV.

According to a further aspect of the present invention there is provided a nucleotide sequence selected from:
(a) the nucleotide sequence presented as any one of SEQ ID NO:2, 4, or 6;
(b) a nucleotide sequence that is a variant, homologue, derivative or fragment of the nucleotide sequence presented as any one of SEQ ID NO:2, 4, or 6;
(c) a nucleotide sequence that is the complement of the nucleotide sequence set out in any one of SEQ ID NO:2, 4, or 6;
(d) a nucleotide sequence that is the complement of a variant, homologue, derivative or fragment of the nucleotide sequence presented as any one of SEQ ID NO:2, 4, or 6;
(e) a nucleotide sequence that is capable of hybridising to the nucleotide sequence set out in any one of SEQ ID NO:2, 4, or 6;
(f) a nucleotide sequence that is capable of hybridising to a variant, homologue, derivative or fragment of the nucleotide sequence presented as any one of SEQ ID NO:2, 4, or 6;
(g) a nucleotide sequence that is the complement of a nucleotide sequence that is capable of hybridising to the nucleotide sequence set out in any one of SEQ ID NO:2, 4, or 6;
(h) a nucleotide sequence that is the complement of a nucleotide sequence that is capable of hybridising to a variant, homologue, derivative or fragment of the nucleotide sequence presented as any one of SEQ ID NO:2, 4, or 6;
(i) a nucleotide sequence that is capable of hybridising to the complement of the nucleotide sequence set out in any one of SEQ ID NO:2, 4, or 6;
(j) a nucleotide sequence that is capable of hybridising to the complement of a variant, homologue, derivative or fragment of the nucleotide sequence presented as any one of SEQ ID NO:2, 4, or 6;
(k) a nucleotide sequence which is degenerate as a result of the genetic code to the nucleotides defined in (a), (b), (c), (d), (e), (f), (g), (h), (i), or (j);
(l) a nucleotide sequence comprising any one of (a), (b), (c), (d), (e), (f), (g), (h), (i), (j) and/or (k).

Other aspects of the present invention are now presented below.

An isolated nucleotide sequence or an isolated protein sequence according to the present invention.

A substantially pure nucleotide sequence or a substantially pure protein sequence according to the present invention.

An assay method for identifying an agent that can affect the expression pattern of the nucleotide sequence of the present invention or the activity of the expression product thereof, the assay method comprising: exposing the nucleotide sequence of the present invention or the expression product ("EP") thereof with an agent; determining whether the agent modulates (such as affects the expression pattern or activity) the nucleotide sequence of the present invention or the expression product thereof.

An agent identified by the assay method of the present invention.

An agent identified by the assay method of the present invention, which agent has hitherto been unknown to have a PDE modulation effect in accordance with the present invention.

A process comprising the steps of: (a) performing the assay of the present invention; (b) identifying one or more agents that affect the expression pattern of the nucleotide sequence of the present invention or the activity of the expression product thereof; (c) preparing a quantity of those one or more identified agents.

A process comprising the steps of: (a) performing the assay according to the present invention; (b) identifying one or more agents that affect the expression pattern of the nucleotide sequence of the present invention or the activity of the expression product thereof; (c) preparing a pharmaceutical composition comprising one or more identified agents.

A process comprising the steps of: (a) performing the assay according to the present invention; (b) identifying one or more agents that affect the expression pattern of the nucleotide sequence of the present invention or the activity of the expression product thereof; (c) modifying one or more identified agents to cause a different effect on the expression pattern of the nucleotide sequence of the present invention or the activity of the expression product thereof.

Use of an agent identified by an assay according to the present invention in the manufacture of a medicament which affects the expression pattern of the nucleotide sequence of the present invention or the activity of the expression product thereof.

A method of treating a target (which target can be a mammal, preferably a human), which method comprises delivering (such as administering or exposing) to the target an effective amount of an agent capable of modulating the expression pattern of the nucleotide sequence of the present invention or the activity of the expression product thereof.

A method of treating a target (which target can be a mammal, preferably a human), which method comprises delivering (such as administering or exposing) to the target an effective amount of an agent identified by an assay according to the present invention.

A method of inducing an immunological response in a subject, the method comprising administering to the subject the nucleotide sequence of the present invention or the expression product thereof.

PDE_XIV

As explained above, the present invention relates to a novel PDE enzyme—which we have called PDE_XIV—and to a nucleotide sequence encoding same. The present invention also relates to the use of the novel nucleic acid and amino acid sequences in the diagnosis and treatment of disease. The present invention also relates to the use of the novel nucleic acid and amino acid sequences to evaluate and/or to screen for agents that can modulate phosphodiesterase activity. The present invention further relates to genetically engineered host cells that comprise or express the novel nucleic acid and amino acid sequences to evaluate and/or to screen for agents that can modulate phosphodiesterase activity.

As used herein, the term "PDE_XIV" refers to a novel family of PDEs which, up until now, were uncharacterised.

By way of example, we have identified a human PDE_XIV (sometimes referred to as HSPDE_XIV). We have also identified a mouse sequence—which we have called PDE_XIV (sometimes referred to as MMPDE_XIV).

For convenience, and unless otherwise stated, reference to PDE_XIV will include reference to HSPDE_XIV and/or MMPDE_XIV.

PDE_XIV is believed to be present in, and obtainable from, a variety of sources.

By way of example, PDE_XIV is found in any one or more of the putamen, the Caudate nucleus of the brain, the Occipital lobe of the brain, the heart, ovary, the pituitary gland, kidney, liver, small intestine, thymus, skeletal muscle, leukocyte regions, dorsal root ganglia, uterus, cochlea, small intestine (duodenum), astrocytoma, and appendix.

We also believe that PDE_XIV is also present in a number of other sources—such as for example: rat, bovine, ovine, porcine, and equine.

Preferably, the present invention covers mammalian PDE_XIV which includes but is not limited to any of the above sources.

More preferably, the present invention covers human PDE_XIV.

The PDE_XIV may be the same as the naturally occurring form—for this aspect, preferably the PDE_XIV is the non-native amino acid sequence (i.e. it is not present in its natural environment)—or is a variant, homologue, fragment or derivative thereof. In addition, or in the alternative, the PDE_XIV is isolated PDE_XIV and/or purified PDE_XIV. The PDE_XIV can be obtainable from or produced by any suitable source, whether natural or not, or it may be synthetic, semi-synthetic or recombinant.

The PDE_XIV coding sequence may be the same as the naturally occurring form—for this aspect, preferably the PDE_XIV coding sequence is the non-native nucleotide sequence (i.e. it is not present in its natural environment)—or is a variant, homologue, fragment or derivative thereof. In addition, or in the alternative, the PDE_XIV coding sequence is an isolated PDE_XIV coding sequence and/or a purified PDE_XIV coding sequence. The PDE_XIV coding sequence can be obtainable from or produced by any suitable source, whether natural or not, or it may be synthetic, semi-synthetic or recombinant.

PDE_XIV and/or its coding sequence and/or a sequence capable of hybridising thereto is/are useful for testing the selectivity of drug candidates between different PDEs.

PDE_XIV is believed to be able to catalyse the conversion of cAMP to AMP.

Preferred aspects of the present invention include a recombinant PDE_XIV enzyme and a recombinant nucleotide sequence encoding a PDE_XIV enzyme.

Preferably the recombinant PDE_XIV enzyme and/or the recombinant nucleotide sequence of the present invention are a recombinant mammalian PDE_XIV enzyme and/or a recombinant mammalian nucleotide sequence.

Preferably the recombinant PDE_XIV enzyme and/or the recombinant nucleotide sequence of the present invention are a recombinant human PDE_XIV enzyme and/or a recombinant human nucleotide sequence.

In accordance with the present invention, the recombinant PDE_XIV enzyme has at least the formula presented as Formula I.

Either or both of the nucleotide sequence coding for PDE_XIV or the enzyme PDE_XIV itself may be used to screen for agents that can affect PDE_XIV activity. In particular, the nucleotide sequence coding for PDE_XIV or PDE_XIV itself may be used to screen for agents that can inhibit PDE_XIV activity. In addition, the nucleotide sequence coding for PDE_XIV or the enzyme PDE_XIV itself may be used to screen for agents that selectively affect PDE_XIV activity, such as selectively inhibit PDE_XIV activity.

Furthermore, the nucleotide sequence coding for PDE_XIV or a sequence that is complementary thereto may also be used in assays to detect the presence of PDE_XIV coding sequences in human cells. These assays would provide information regarding the tissue distribution of this enzyme and its biological relevance with respect to particular disease states.

The present invention also covers antibodies to PDE_XIV (including a derivative, fragment, homologue or variant thereof). The antibodies for PDE_XIV may be used in assays to detect the presence of PDE_XIV in human cells. These assays would provide information regarding the tissue distribution of this enzyme and its biological relevance with respect to particular disease states.

In particular, any one or more of PDE_XIV isozymes, the nucleotide sequences coding for same, the nucleotide sequences that are complementary to same, and the antibodies directed to same may be used in assays to screen for agents that selectively affect one of the isozymes. These assays would provide information regarding the tissue distribution of each of the isozymes and to provide information regarding the biological relevance of each of the isozymes with respect to particular disease states. These assays would also allow workers to test for and identify agents that are useful to affect the expression of or activity of PDE_XIV—such as in a particular tissue or in a particular disease state.

POLYPEPTIDE of the PRESENT INVENTION

The term "polypeptide"—which is interchangeabe with the term "protein"—includes single-chain polypeptide molecules as well as multiple-polypeptide complexes where individual constituent polypeptides are linked by covalent or non-covalent means.

Preferably, the polypeptide of the present invention is a single-chain polypeptide.

Polypeptides of the present invention may be in a substantially isolated form. It will be understood that the polypeptide may be mixed with carriers or diluents which will not interfere with the intended purpose of the polypeptide and still be regarded as substantially isolated. A polypeptide of the present invention may also be in a substantially purified form, in which case it will generally comprise the polypeptide in a preparation in which more than 90%, e.g. 95%, 98% or 99% of the polypeptide in the preparation is a polypeptide of the present invention. Polypeptides of the present invention may be modified for example by the addition of histidine residues to assist their purification or by the addition of a signal sequence to promote their secretion from a cell as discussed below.

Polypeptides of the present invention may be produced by synthetic means (e.g. as described by Geysen et al., 1996) or recombinantly, as described below.

In a preferred embodiment, the amino acid sequence per se the present invention does not cover the native PDE_XIV according to the present invention when it is in its natural environment and when it has been expressed by its native nucleotide coding sequence which is also in its natural environment and when that nucleotide sequence is under the control of its native promoter which is also in its natural environment. For ease of reference, we have called this preferred embodiment the "non-native amino acid sequence".

The terms "variant", "homologue" or "fragment" in relation to the amino acid sequence for the enzyme of the present invention include any substitution of, variation of, modification of, replacement of, deletion of or addition of one (or more) amino acid from or to the sequence providing the resultant enzyme has PDE_XIV activity, preferably being at least as biologically active as the enzyme shown in the attached sequence listings. In particular, the term "homologue" covers homology with respect to structure and/or function. With respect to sequence homology, preferably there is at least 75%, more preferably at least 85%, more preferably at least 90% homology to the sequence shown as Formula I. More preferably there is at least 95%, more preferably at least 98%, homology to the sequence shown as Formula I. More preferably there is at least 75%, more preferably at least 85%, more preferably at least 90% homology to any one of the sequences shown in the attached sequence listings. More preferably there is at least 95%, more preferably at least 98%, homology to any one of the sequence shown as shown in the attached sequence listings.

Typically, the types of amino acid substitutions that could be made should maintain the hydrophobicity/hydrophilicity of the amino acid sequence. Amino acid substitutions may be made, for example from 1, 2 or 3 to 10, 20 or 30 substitutions provided that the modified sequence retains the ability to act as a PDE enzyme in accordance with present invention. Amino acid substitutions may include the use of non-naturally occurring analogues, for example to increase blood plasma half-life.

The amino acid sequence of the present invention may be produced by expression of a nucleotide sequence coding for same in a suitable expression system.

In addition, or in the alternative, the protein itself could be produced using chemical methods to synthesize a PDE amino acid sequence, in whole or in part. For example, peptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure).

Direct peptide synthesis can be performed using various solid-phase techniques (Roberge J Y et al (1995) Science 269: 202–204) and automated synthesis may be achieved, for example, using the ABI 43 1 A Peptide Synthesizer (Perkin Elmer) in accordance with the instructions provided by the manufacturer. Additionally, the amino acid sequence of PDE, or any part thereof, may be altered during direct synthesis and/or combined using chemical methods with a sequence from other subunits, or any part thereof, to produce a variant polypeptide.

In another embodiment of the invention, a PDE natural, modified or recombinant sequence may be ligated to a heterologous sequence to encode a fusion protein. For example, for screening of peptide libraries for inhibitors of PDE activity, it may be useful to encode a chimeric PDE protein expressing a heterologous epitope that is recognised by a commercially available antibody. A fusion protein may also be engineered to contain a cleavage site located between a PDE sequence and the heterologous protein sequence, so that the PDE may be cleaved and purified away from the heterologous moiety.

PDE may also be expressed as a recombinant protein with one or more additional polypeptide domains added to facilitate protein purification. Such purification facilitating domains include, but are not limited to, metal chelating peptides such as histidine-tryptophan modules that allow purification on immobilised metals (Porath J (1992) Protein Expr Purif 3-.26328 1), protein A domains that allow purification on immobilised immunoglobulin, and the domain utilised in the FLAGS extension/affinity purification system (Immunex Corp, Seattle, Wash.). The inclusion of a cleavable linker sequence such as Factor XA or enterokinase (Invitrogen, San Diego, Calif.) between the purification domain and PDE is useful to facilitate purification. In a preferred aspect, the enzyme is expressed with a FLAG epitope tag in order to facilitate isolation and purification of the expressed enzyme.

Specific amino acid sequences of PDE_XIV are shown as SEQ ID NO:1 and SEQ ID NO:3 and SEQ ID NO:5. However, the present invention encompasses amino acid sequences encoding other members from the PDE_XIV family which would include amino acid sequences having at least 60% identity (more preferably at least 75% identity) to any one of the amino acid sequences. As indicated, suitable generic formulae for the PDE_XIV family in accordance with the present invention are presented as Formula I.

Polypeptides of the present invention also include fragments of the presented amino acid sequence and variants thereof. Suitable fragments will be at least 5, e.g. at least 10, 12, 15 or 20 amino acids in size.

Polypeptides of the present invention may also be modified to contain one or more (e.g. at least 2, 3, 5, or 10) substitutions, deletions or insertions, including conserved substitutions. These aspects are discussed in a later section.

Nucleotide Sequence of the Present Invention

The term "nucleotide sequence" as used herein refers to an oligonucleotide sequence or polynucleotide sequence, and variants, homologues, fragments and derivatives thereof (such as portions thereof). The nucleotide sequence may be DNA or RNA which may be of genomic or synthetic or recombinant origin which may be double-stranded or single-stranded whether representing the sense or antisense strand.

Preferably, the term "nucleotide sequence" means DNA. More preferably, the term "nucleotide sequence" means DNA prepared by use of recombinant DNA techniques (i.e. recombinant DNA).

In a preferred embodiment, the nucleotide sequence per se of the present invention does not cover the native nucleotide coding sequence according to the present invention in its natural environment when it is under the control of its native promoter which is also in its natural environment. For ease of reference, we have called this preferred embodiment the "non-native nucleotide sequence".

The nucleotide sequences of the present invention may include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art. Such modifications may be carried out in to enhance the in vivo activity or life span of nucleotide sequences of the present invention.

The present invention also encompasses nucleotide sequences that are complementary to the sequences presented herein, or any derivative, fragment or derivative thereof. If the sequence is complementary to a fragment thereof then that sequence can be used a probe to identify similar coding sequences in other organisms etc.

The present invention also encompasses nucleotide sequences that are capable of hybridising to the sequences presented herein, or any derivative, fragment or derivative thereof.

The present invention also encompasses nucleotide sequences that are capable of hybridising to the sequences that are complementary to the sequences presented herein, or any derivative, fragment or derivative thereof.

The term "variant" also encompasses sequences that are complementary to sequences that are capable of hydridising to the nucleotide sequences presented herein.

Preferably, the term "variant" encompasses sequences that are complementary to sequences that are capable of hydridising under stringent conditions (e.g. 55° C. and 0.2×SSC {1×SSC=0.15 M NaCl, 0.015 Na$_3$ citrate pH 7.0}) to the nucleotide sequences presented herein.

More preferably, the term "variant" encompasses sequences that are complementary to sequences that are capable of hydridising under high stringent conditions (e.g. 65° C. and 0.1×SSC {1×SSC=0.15 M NaCl, 0.015 Na$_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 55° C. and 0.2×SSC).

In a more preferred aspect, the present invention covers nucleotide sequences that can hybridise to the nucleotide sequence of the present invention, or the complement thereof, under high stringent conditions (e.g. 65° C. and 0.1×SSC).

Exemplary nucleic acids can alternatively be characterised as those nucleotide sequences which encode a PDE_XIV protein and hybridise to any one or more of the DNA sequences shown in the attached sequence listings. Preferred are such sequences encoding PDE_XIV which hybridise under high-stringency conditions to any one of the sequences shown in the attached sequence listings or the complement thereof.

Advantageously, the invention provides nucleic acid sequences which are capable of hybridising, under stringent conditions, to a fragment of any one of the sequences shown in the attached sequence listings or the complement thereof. Preferably, the fragment is between 15 and 50 bases in length. Advantageously, it is about 25 bases in length.

The terms "variant", "homologue" or "fragment" in relation to the nucleotide sequence coding for the preferred enzyme of the present invention include any substitution of, variation of, modification of, replacement of, deletion of or addition of one (or more) nucleic acid from or to the sequence providing the resultant nucleotide sequence codes for or is capable of coding for an enzyme having PDE_XIV activity, preferably being at least as biologically active as the enzyme encoded by any one of the sequences shown in the attached sequence listings. In particular, the term "homologue" covers homology with respect to structure and/or function providing the resultant nucleotide sequence codes for or is capable of coding for an enzyme having PDE_XIV activity. With respect to sequence homology, preferably there is at least 75%, more preferably at least 85%, more preferably at least 90% homology to a nucleotide sequence coding for the amino acid sequence shown as Formula I. More preferably there is at least 95%, more preferably at least 98% homology to a nucleotide sequence coding for the amino acid sequence shown as Formula I. Preferably, with respect to sequence homology, preferably there is at least 75%, more preferably at least 85%, more preferably at least 90% homology to any one of the sequences shown in the attached sequence listings. More preferably there is at least 95%, more preferably at least 98%, homology to any one of the sequences shown in the attached sequence listings.

As indicated, the present invention relates to a DNA sequence (preferably a cDNA sequence) encoding PDE_XIV. In particular, the present invention relates to cDNA sequences encoding PDE_XIV.

The present invention also relates to DNA segments comprising the DNA sequence of any one of the sequences shown in the attached sequence listings or allelic variations of such sequences.

The present invention also relates to polypeptides produced by expression in a host cell into which has been incorporated the foregoing DNA sequences or allelic variations thereof.

The present invention also relates provides DNA comprising the DNA sequence of any one of the sequences shown in the attached sequence listings or an allelic variation thereof.

The present invention also relates to non-native DNA comprising the DNA sequence of any one of the sequences shown in the attached sequence listings or an allelic variation thereof.

A highly preferred aspect of the present invention relates to recombinant DNA comprising the DNA sequence of any one of the sequences shown in the attached sequence listings or an allelic variation thereof.

Polynucleotides of the present invention include nucleotide acid sequences encoding the polypeptides of the present invention. It will appreciated that a range of different polynucleotides encode a given amino acid sequence as a consequence of the degeneracy of the genetic code.

By knowledge of the amino acid sequences set out herein it is possible to devise partial and full-length nucleic acid sequences such as cDNA and/or genomic clones that encode the polypeptides of the present invention. For example, polynucleotides of the present invention may be obtained using degenerate PCR which will use primers designed to target sequences encoding the amino acid sequences presented herein. The primers will typically contain multiple degenerate positions. However, to minimise degeneracy, sequences will be chosen that encode regions of the amino acid sequences presented herein containing amino acids such as methionine which are coded for by only one triplet. In addition, sequences will be chosen to take into account codon usage in the organism whose nucleic acid is used as the template DNA for the PCR procedure. PCR will be used at stringency conditions lower than those used for cloning sequences with single sequence (non-degenerate) primers against known sequences.

Nucleic acid sequences obtained by PCR that encode polypeptide fragments of the present invention may then be used to obtain larger sequences using hybridisation library screening techniques. For example a PCR clone may be labelled with radioactive atoms and used to screen a cDNA or genomic library from other species, preferably other mammalian species. Hybridisation conditions will typically be conditions of medium to high stringency (for example 0.03M sodium chloride and 0.03M sodium citrate at from about 50° C. to about 60° C.).

Degenerate nucleic acid probes encoding all or part of the amino acid sequence may also be used to probe cDNA and/or genomic libraries from other species, preferably other mammalian species. However, it is preferred to carry out PCR techniques initially to obtain a single sequence for use in further screening procedures.

In accordance with the present invention, PDE_XIV polynucleotide sequences which encode PDE_XIV, fragments of the polypeptide, fusion proteins or functional equivalents thereof, may be used to generate recombinant DNA molecules that direct the expression of PDE_XIV in appropriate host cells. Due to the inherent degeneracy of the genetic code, other DNA sequences which encode substantially the same or a functionally equivalent amino acid sequence, may be used to clone and express PDE_XIV. As will be understood by those of skill in the art, it may be advantageous to produce PDE-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of PDE_XIV expression or to produce recombinant RNA transcripts having desirable properties, such as a longer half-life, than transcripts produced from naturally occurring sequence.

Polynucleotide sequences of the present invention obtained using the techniques described above may be used to obtain further homologous sequences and variants using the techniques described above. They may also be modified for use in expressing the polypeptides of the present invention in a variety of host cells systems, for example to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Altered PDE_XIV polynucleotide sequences which may be used in accordance with the invention include deletions, insertions or substitutions of different nucleotide residues resulting in a polynucleotide that encodes the same or a functionally equivalent PDE. The protein may also have deletions, insertions or substitutions of amino acid residues which produce a silent change and result in a functionally equivalent PDE. Deliberate amino acid substitutions may be made on the basis of similarity in polarity, charge, solubility, hydrophobicity, hydrophilicity, and/or the amphipathic nature of the residues as long as the biological activity of PDE is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Included within the scope of the present invention are alleles of PDE. As used herein, an "allele" or "allelic sequence" is an alternative form of PDE. Alleles result from a mutation, i.e., a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The term "allele" also includes genetic polymorphisms, such as SNPs (single nucleotide polymorphisms).

The nucleotide sequences of the present invention may be engineered in order to alter a PDE coding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns or to change codon preference.

Polynucleotides of the present invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the present invention as used herein.

Polynucleotides or primers of the present invention may carry a revealing label. Suitable labels include radioisotopes such as $^{32}P$ or $^{35}S$, enzyme labels, or other protein labels such as biotin. Such labels may be added to polynucleotides or primers of the present invention and may be detected using by techniques known per se.

Polynucleotides such as a DNA polynucleotide and primers according to the present invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15–30 nucleotides) to a region of the nucleotide sequence which it is desired to clone, bringing the primers into contact with mRNA or cDNA obtained from a fungal, plant or prokaryotic cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

As mentioned earlier, the present invention also relates to nucleotide sequences that are capable of hybridising to all or part of any one of the sequences shown in the attached sequence listings or an allelic variation thereof. These nucleotide sequences may be used in anti-sense techniques to modify PDE_XIV expression. Alternatively, these sequences (or portions thereof) can be used as a probe, or for amplifying all or part of such sequence when used as a polymerase chain reaction primer.

In addition to the recombinant DNA sequences, genomic sequences are also of utility in the context of drug discovery. It may be valuable to inhibit the mRNA transcription of a particular isoform rather than to inhibit its translated protein. This may be true with PDE_XIV, if there are splice variants and wherein those different splice variants may be transcribed from different promoters. There is precedent for multiple promoters directing the transcription of a mouse brain 2',3'-cyclic-nucleotide 3' phosphodiesterase (Kurihara T et al., Biochem. Biophys. Res. Comm. 170:1074 [1990]).

Another utility of the invention is that the DNA sequences, once known, give the information needed to design assays to specifically detect isoenzymes or splice variants. Isozyme-specific PCR primer pairs are but one example of an assay that depends completely on the knowledge of the specific DNA sequence of the isozyme or splice variant. Such an assay allows detection of mRNA for the isozyme to access the tissue distribution and biological relevance of each isozyme to a particular disease state. It also allows identification of cell lines that may naturally express only one isozyme—a discovery that might obviate the need to express recombinant genes. If specific PDE_XIV isozymes are shown to associated with a particular disease state, the invention would be valuable in the design of diagnostic assays to detect the presence of isozyme mRNA.

An abnormal level of nucleotide sequences encoding a PDE_XIV in a biological sample may reflect a chromosomal aberration, such as a nucleic acid deletion or mutation. Accordingly, nucleotide sequences encoding a PDE_XIV provide the basis for probes which can be used diagnostically to detect chromosomal aberrations such as deletions, mutations or chromosomal translocations in the gene encoding PDE. PDE_XIV gene expression may be altered in such disease states or there may be a chromosomal aberration present in the region of the gene encoding a PDE_XIV.

In an alternative embodiment of the invention, the coding sequence of PDE could be synthesized, in whole or in part, using chemical methods well known in the art (see Caruthers M H et al (1980) Nuc Acids Res Symp Ser 215–23, Horn T et al (1980) Nuc Acids Res Symp Ser 225–232).

Naturally Occurring

As used herein "naturally occurring" refers to a PDE_XIV with an amino acid sequence found in nature.

Isolated/Purified

As used herein, the terms "isolated" and "purified" refer to molecules, either nucleic or amino acid sequences, that are removed from their natural environment and isolated or separated from at least one other component with which they are naturally associated.

Biologically Active

As used herein "biologically active" refers to a PDE_XIV according to the present invention—such as a recombinant PDE_XIV—having a similar structural function (but not necessarily to the same degree), and/or similar regulatory function (but not necessarily to the same degree), and/or similar biochemical function (but not necessarily to the same degree) and/or immunological activity (but not necessarily to the same degree) of the naturally occurring PDE_XIV. Specifically, a PDE_XIV of the present invention has the ability to hydrolyse a cyclic nucleotide, which is one of the characteristic activities of the PDE enzyme of the present invention.

Immunological Activity

As used herein, "immunological activity" is defined as the capability of the natural, recombinant or synthetic PDE_XIV or any oligopeptide thereof, to induce a specific immune response in appropriate animals or cells and to bind with specific antibodies.

Derivative

The term "derivative" as used herein in relation to the amino acid sequence includes chemical modification of a PDE_XIV. Illustrative of such modifications would be replacement of hydrogen by an alkyl, acyl, or amino group.

Deletion

As used herein a "deletion" is defined as a change in either nucleotide or amino acid sequence in which one or more nucleotides or amino acid residues, respectively, are absent.

Insertion/Addition

As used herein an "insertion" or "addition" is a change in a nucleotide or amino acid sequence which has resulted in the addition of one or more nucleotides or amino acid residues, respectively, as compared to the naturally occurring PDE.

Substitution

As used herein "substitution" results from the replacement of one or more nucleotides or amino acids by different nucleotides or amino acids, respectively.

Homologue

The term "homologue" with respect to the nucleotide sequence of the present invention and the amino acid sequence of the present invention may be synonymous with allelic variations of the sequences.

In particular, the term "homology" as used herein may be equated with the term "identity". Here, sequence homology with respect to the nucleotide sequence of the present invention and the amino acid sequence of the present invention can be determined by a simple "eyeball" comparison (i.e. a strict comparison) of any one or more of the sequences with another sequence to see if that other sequence has at least 75% identity to the sequence(s). Relative sequence homology (i.e. sequence identity) can also be determined by commercially available computer programs that can calculate % homology between two or more sequences. A typical example of such a computer program is CLUSTAL.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for off-line and on-line searching (see Ausubel et al., 1999 ibid, pages 7-58 to 7-60). However, for some applications it is preferred to use the GCG Besffit program.

Although the final % homology can be measured in terms of identity, in some cases, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix— the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

As indicated, for some applications, sequence homology (or identity) may be determined using any suitable homology algorithm, using for example default parameters.

Advantageously, the BLAST algorithm is employed, with parameters set to default values. The BLAST algorithm is described in detail at http://www.ncbi.nih.gov/BLAST/blast_help.html. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see http://www.ncbi.nih.gov/BLAST/blast_help.html) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al (1994) Nature Genetics 6:119–129.

The five BLAST programs available at http://www.ncbi.nlm.nih.gov perform the following tasks:

blastp compares an amino acid query sequence against a protein sequence database;

blastn compares a nucleotide query sequence against a nucleotide sequence database;

blastx compares the six-frame conceptual translation products of a nucleotide query sequence (both strands) against a protein sequence database;

tblastn compares a protein query sequence against a nucleotide sequence database dynamically translated in all six reading frames (both strands).

tblastx compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149–163, or segments consisting of short-periodicity internal repeats, as determined by the XNU program of Claverie & States (1993) Computers and Chemistry 17:191–201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

Most preferably, sequence comparisons are conducted using the simple BLAST search algorithm provided at http://www.ncbi.nlm.nih.gov/BLAST.

Should Gap Penalties be used when determining sequence identity, then preferably the following parameters are used:

| FOR BLAST | |
| --- | --- |
| GAP OPEN | 0 |
| GAP EXTENSION | 0 |

| -continued | | |
| --- | --- | --- |
| FOR CLUSTAL | DNA | PROTEIN |
| WORD SIZE | 2 | 1 K triple |
| GAP PENALTY | 10 | 10 |
| GAP EXTENSION | 0.1 | 0.1 |

Other computer program methods to determine identify and similarity between the two sequences include but are not limited to the GCG program package (Devereux et al 1984 Nucleic Acids Research 12: 387 and FASTA (Atschul et al 1990 J Molec Biol 403–410).

Polypeptide Variants and Derivatives

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has PDE activity, preferably having at least the same activity as any one of the polypeptides presented in the sequence listings.

The sequences of the present invention may be modified for use in the present invention. Typically, modifications are made that maintain the PDE activity of the sequence. Amino acid substitutions may be made, for example from 1, 2 or 3 to 10, 20 or 30 substitutions provided that the modified sequence retains the PDE activity. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | G A P |
| --- | --- | --- |
| | | I L V |
| | Polar-uncharged | C S T M |
| | | N Q |
| | Polar-charged | D E |
| | | K R |
| AROMATIC | | H F W Y |

As indicated above, proteins of the invention are typically made by recombinant means, for example as described herein, and/or by using synthetic means using techniques well known to skilled persons such as solid phase synthesis. Varaiants and derivatives of such sequences include fusion proteins, wherein the fusion proteins comprise at least the amino acid sequence of the present invention being linked (directly or indirectly) to another amino acid sequence. These other amino acid sequences—which are sometimes referred to as fusion protein partners—will typically impart a favourable functionality—such as to aid extraction and purification of the amino acid sequence of the present invention. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of the present invention so as to allow removal of the latter. Preferably the fusion protein partner will not hinder the function of the protein of the present invention.

Polynucleotide Variants and Derivatives

The terms "variant" or "derivative" in relation to the nucleotide sequence of the present invention include any substitution of, variation of, modification of, replacement of, deletion of or addition of one (or more) nucleic acid from or to the sequence providing the resultant nucleotide sequence codes for a polypeptide having PDE activity, preferably having at least the same activity as sequences presented in the sequence listings.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. For some applications, a preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

As used herein, the terms "variant", "homologue", "fragment" and "derivative" embrace allelic variations of the sequences.

The term "variant" also encompasses sequences that are complementary to sequences that are capable of hydridising to the nucleotide sequences presented herein.

Hybridisation

The term "hybridisation" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65–68° C.

Maximum stringency typically occurs at about Tm−5° C. (5° C. below the Tm of the probe). High stringency at about 5° C. to 10° C. below the Tm of the probe. High stringency conditions can be provided, for example, by hybridisation in an aqueous solution containing 6×SSC, 5×Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1×SSC, 0.1% SDS.

Moderate, or intermediate, stringency typically occurs at about 10° C. to 20° C. below the Tm of the probe.

Low stringency typically occurs at about 20° C. to 25° C. below the Tm of the probe.

As will be understood by those of skill in the art, a maximum stringency hybridisation can be used to identify or detect identical polynucleotide sequences while an intermediate (or low) stringency hybridisation can be used to identify or detect similar or related polynucleotide sequences.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 50–52° C. In that case, the final wash is performed at the hybridisation temperature in 2×SSC, 0.1% SDS.

For some applications, it may be useful to use low to medium stringent conditions to identify similar enzymes coding sequences from different organisms.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Polynucleotides of the invention capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridisable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

In a preferred aspect, the present invention covers nucleotide sequences that can hybridise to any one or more of the nucleotide sequences of the present invention under stringent conditions (e.g. 60° C. and 0.2×SSC {1×SSC=0.15 M NaCl, 0.015 M $Na_3$ Citrate pH 7.0).

In a more preferred aspect, the present invention covers nucleotide sequences that can hybridise to any one or more of the nucleotide sequences of the present invention under high stringent conditions (e.g. 65° C. and 0.1×SSC {1×SSC=0.15 M NaCl, 0.015 M $Na_3$ Citrate pH 7.0).

Where the polynucleotide of the present invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Regulatory Sequences

Preferably, the polynucleotide of the present invention is operably linked to a regulatory sequence which is capable of providing for the expression of the coding sequence, such as by the chosen host cell. By way of example, the present invention covers a vector comprising the polynucleotide of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the polynucleotide encoding the polypeptide of the present invention may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the polypeptide of the present invention Preferably, the nucleotide sequence of the present invention may be operably linked to at least a promoter.

Aside from the promoter native to the gene encoding the polypeptide of the present invention, other promoters may be used to direct expression of the polypeptide of the present invention. The promoter may be selected for its efficiency in directing the expression of the polypeptide of the present invention in the desired expression host.

In another embodiment, a constitutive promoter may be selected to direct the expression of the desired polypeptide of the present invention. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

Secretion

Often, it is desirable for the polypeptide of the present invention to be secreted from the expression host into the culture medium from where the polypeptide of the present invention may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces* and *Kluyveromyces*) or the α-amylase gene (*Bacillus*).

Constructs

The term "construct"—which is synonymous with terms such as "conjugate", "cassette" and "hybrid"—includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In each case, the terms do not cover the natural combination of the nucleotide sequence coding for the protein ordinarily associated with the wild type gene promoter and when they are both in their natural environment.

The construct may even contain or express a marker which allows for the selection of the genetic construct in, for example, a bacterium, preferably of the genus *Bacillus*, such as *Bacillus subtilis*, or plants into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

Preferably the construct of the present invention comprises at least the nucleotide sequence of the present invention operably linked to a promoter.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *E.coli* plasmid to a bacterium, such as of the genus *Bacillus*, then the transformation vector is sometimes called a "shuttle vector". It may even be a construct capable of being transferred from an *E.coli* plasmid to an *Agrobacterium* to a plant.

The vectors of the present invention may be transformed into a suitable host cell as described below to provide for expression of a polypeptide of the present invention. Thus, in a further aspect the invention provides a process for preparing polypeptides according to the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter.

The vectors of the present invention may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in filamentous fungi), the ampicillin resistance gene (*E. coli*), the neomycin resistance gene (*Bacillus*) and the *E.coli* uidA gene, coding for β-glucuronidase (GUS).

Vectors may be used in vitro, for example for the production of RNA or used to transfect or transform a host cell.

Thus, polynucleotides of the present invention can be incorporated into a recombinant vector (typically a replicable vector), for example a cloning or expression vector. The vector may be used to replicate the nucleic acid in a compatible host cell. Thus in a further embodiment, the invention provides a method of making polynucleotides of the present invention by introducing a polynucleotide of the present invention into a replicable vector, introducing the vector into a compatible host cell, and growing the host cell under conditions which bring about replication of the vector. The vector may be recovered from the host cell. Suitable host cells are described below in connection with expression vectors.

The present invention also relates to the use of genetically engineered host cells expressing a PDE_XIV or variant, homologue, fragment or derivative thereof in screening methods for the identification of inhibitors and antagonists of the PDE_XIV that would modulate phosphodiesterase activity thereby modulating cyclic nucleotide levels. Such genetically engineered host cells could be used to screen peptide libraries or organic molecules capable of modulating PDE_XIV activity. Antagonists and inhibitors of PDE_XIV, such as antibodies, peptides or small organic molecules will provide the basis for pharmaceutical compositions for the treatment of diseases associated with, for example, PDE_XIV. Such inhibitors or antagonists can be administered alone or in combination with other therapeutics for the treatment of such diseases.

The present invention also relates to expression vectors and host cells comprising polynucleotide sequences encoding PDE_XIV or variant, homologue, fragment or derivative thereof for the in vivo or in vitro production of PDE_XIV protein or to screen for agents that can affect PDE_XIV expression or activity.

Tissue

The term "tissue" as used herein includes tissue per se and organ.

Host Cells

The term "host cell"—in relation to the present invention includes any cell that could comprise the nucleotide sequence coding for the recombinant protein according to the present invention and/or products obtained therefrom, wherein a promoter can allow expression of the nucleotide sequence according to the present invention when present in the host cell.

Thus, a further embodiment of the present invention provides host cells transformed or transfected with a polynucleotide of the present invention. Preferably said polynucleotide is carried in a vector for the replication and expression of said polynucleotides. The cells will be chosen to be compatible with the said vector and may for example be prokaryotic (for example bacterial), fungal, yeast or plant cells.

The gram-negative bacterium *E. coli* is widely used as a host for heterologous gene expression. However, large amounts of heterologous protein tend to accumulate inside the cell. Subsequent purification of the desired protein from the bulk of *E.coli* intracellular proteins can sometimes be difficult.

In contrast to *E.coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the nucleotide sequence coding for the recombinant protein according to the present invention and/or products obtained therefrom, wherein a promoter can allow expression of the nucleotide sequence according to the present invention when present in the organism. Examples of organisms may include a fungus, yeast or a plant.

The term "transgenic organism" in relation to the present invention includes any organism that comprises the nucleotide sequence coding for the protein according to the present invention and/or products obtained therefrom, wherein the promoter can allow expression of the nucleotide sequence according to the present invention within the organism. Preferably the nucleotide sequence is incorporated in the genome of the organism.

The term "transgenic organism" does not cover the native nucleotide coding sequence according to the present invention in its natural environment when it is under the control of its native promoter which is also in its natural environment. In addition, the present invention does not cover the native protein according to the present invention when it is in its natural environment and when it has been expressed by its native nucleotide coding sequence which is also in its natural environment and when that nucleotide sequence is under the control of its native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, tissues according to the present invention or the products thereof. The transformed cell or organism could prepare acceptable quantities of the desired compound which would be easily retrievable from, the cell or organism.

The present invention also encompasses organisms that have been modified so that they express elevated levels of the enzyme.

Attenuation/Knock-Out Animal Models

The present invention also encompasses organims that have been modified so that the enzyme activity has been attenuated or even eliminated. An example of such an embodiment is a knock-out rat or mouse wherein the natural coding sequence has been removed and replaced with, for example, a reporter gene—such as β-gal. Alternatively, the promoter can be silenced so that no gene expression occurs. These types of organisms may be prepared by use of standard techniques.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-industry Hi-Tech March/April 1994 17–27). Further teachings on plant transformation may be found in EP-A-0449375.

Thus, the present invention also provides a method of transforming a host cell with a nucleotide sequence shown as any one of the sequences shown in the attached sequence listings or a derivative, homologue, variant or fragment thereof.

Host cells transformed with a PDE nucleotide coding sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing PDE coding sequences can be designed with signal sequences which direct secretion of PDE coding sequences through a particular prokaryotic or eukaryotic cell membrane. Other recombinant constructions may join PDE coding sequence to nucleotide sequence encoding a polypeptide domain which will facilitate purification of soluble proteins (Kroll D J et al (1993) DNA Cell Biol 12:441–53, see also above discussion of vectors containing fusion proteins).

Production of the Polypeptide

According to the present invention, the production of the polypeptide of the present invention can be effected by the culturing of, for example, microbial expression hosts, which have been transformed with one or more polynucleotides of the present invention, in a conventional nutrient fermentation medium. The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating micro-organisms.

Thus, the present invention also provides a method for producing a polypeptide having PDE_XIV activity, the method comprising the steps of a) transforming a host cell with a nucleotide sequence shown as any one of the sequences shown in the attached sequence listings or a derivative, homologue, variant or fragment thereof; and b) culturing the transformed host cell under conditions suitable for the expression of said polypeptide.

The present invention also provides a method for producing a polypeptide having PDE_XIV activity, the method comprising the steps of a) culturing a host cell that has been transformed with a nucleotide sequence shown as any one of the sequences shown in the attached sequence listings or a derivative, homologue, variant or fragment thereof under conditions suitable for the expression of said polypeptide; and b) recovering said polypeptide from the host cell culture.

The present invention also provides a method for producing a polypeptide having PDE_XIV activity, the method comprising the steps of a) transforming a host cell with a nucleotide sequence shown as any one of the sequences shown in the attached sequence listings or a derivative, homologue, variant or fragment thereof; b) culturing the transformed host cell under conditions suitable for the expression of said polypeptide; and c) recovering said polypeptide from the host cell culture.

Ribozymes

Ribozymes are enzymatic RNA molecules capable of catalysing the specific cleavage of RNA. The mechanism of ribozyme action involves sequence specific hybridisation of the ribozyme molecule to complementary target RNA, followed by a endonucleolytic cleavage. Within the scope of the invention are engineered hammerhead motif ribozyme molecules that specifically and efficiently catalyse endonucleolytic cleavage of PDE RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridisation with complementary oligonucleotides using ribonuclease protection assays.

Both antisense RNA and DNA molecules and ribozymes of the invention may be prepared by any method known in the art for the synthesis of RNA molecules. These include techniques for chemically synthesising oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

Detection

The presence of the PDE polynucleotide coding sequence can be detected by DNA-DNA or DNA-RNA hybridisation or amplification using probes, portions or fragments of the sequence presented as any one of the sequences shown in the attached sequence listings. Nucleic acid amplification based assays involve the use of oligonucleotides or oligomers based on the PDE coding sequence to detect transformants containing PDE DNA or RNA. As used herein "oligonucleotides" or "oligomers" may refer to a nucleic acid sequence of at least about 10 nucleotides and as many as about 60 nucleotides, preferably about 15 to 30 nucleotides, and more preferably about 20–25 nucleotides which can be used as a probe or amplimer. Preferably, oligonucleotides are derived from the 3' region of the nucleotide sequence shown as any one of the sequences shown in the attached sequence listings.

A variety of protocols for detecting and measuring the expression of PDE polypeptide, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on PDE polypeptides is preferred, but a competitive binding assay may be employed. These and other assays are described, among other places, in Hampton R et al (1990, Serological Methods, A Laboratory Manual, APS Press, St Paul Minn.) and Maddox D E et al (1983, J Exp Med 15 8:121 1).

A wide variety of labels and conjugation techniques are known by those skilled in the art and can be used in various nucleic and amino acid assays. Means for producing labelled hybridisation or PCR probes for detecting PDE polynucleotide sequences include oligolabelling, nick translation, end-labelling or PCR amplification using a labelled nucleotide. Alternatively, the PDE coding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241. Also, recombinant immunoglobulins may be produced as shown in U.S. Pat. No. 4,816,567.

Additional methods to quantify the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Although the presence/absence of marker gene expression suggests that the gene of interest is also present, its presence and expression should be confirmed. For example, if the PDE coding sequence is inserted within a marker gene sequence, recombinant cells containing PDE coding regions can be identified by the absence of marker gene function. Alternatively, a marker gene can be placed in tandem with a PDE coding sequence under the control of a single promoter. Expression of the marker gene in response to induction or selection usually indicates expression of PDE as well.

Alternatively, host cells which contain the coding sequence for PDE and express PDE coding regions may be identified by a variety of procedures known to those of skill in the art. These procedures include, but are not limited to, DNA-DNA or DNA-RNA hybridisation and protein bioassay or immunoassay techniques which include membrane-based, solution-based, or chip-based technologies for the detection and/or quantification of the nucleic acid or protein.

Antibodies

The amino acid sequence of the present invention can also be used to generate antibodies—such as by use of standard techniques—against the amino acid sequence.

Procedures well known in the art may be used for the production of antibodies to PDE_XIV polypeptides. Such antibodies include, but are not limited to, polyclonal, monoclonal, chimeric, single chain, Fab fragments and fragments produced by a Fab expression library. Neutralising antibodies, i.e., those which inhibit biological activity of PDE polypeptides, are especially preferred for diagnostics and therapeutics.

For the production of antibodies, various hosts including goats, rabbits, rats, mice, etc. may be immunised by injection with the inhibitor or any portion, variant, homologue, fragment or derivative thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacilli Calmette-Guerin*) and *Corynebacterium parvum* are potentially useful human adjuvants which may be employed.

Monoclonal antibodies to the amino acid sequence may be even prepared using any technique which provides for the production of antibody molecules by continuous cell lines in culture. These include, but are not limited to, the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,779) can be adapted to produce inhibitor specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for PDE_XIV may also be generated. For example, such fragments include, but are not limited to, the F(ab')$_2$ fragments which can be produced by pepsin digestion of the antibody molecule and the Fab fragments which can be generated by reducing the disulphide bridges of the F(ab')$_2$ fragments. Alternatively, Fab expression libraries may be constructed to allow rapid and easy identification of monoclonal Fab fragments with the desired specificity (Huse W D et al (1989) Science 256:1275–128 1).

An alternative technique involves screening phage display libraries where, for example the phage express scFv fragments on the surface of their coat with a large variety of complementarity determining regions (CDRs). This technique is well known in the art.

PDE_XIV-specific antibodies are useful for the diagnosis of conditions and diseases associated with expression of PDE_XIV polypeptide. A variety of protocols for competitive binding or immunoradiometric assays using either polyclonal or monoclonal antibodies with established specificities are well known in the art. Such immunoassays typically involve the formation of complexes between PDE_XIV polypeptides and its specific antibody (or similar PDE_XIV-binding molecule) and the measurement of complex formation. A two-site, monoclonal based immunoassay utilising monoclonal antibodies reactive to two non-interfering epitopes on a specific PDE_XIV protein is preferred, but a competitive binding assay may also be employed. These assays are described in Maddox D E et al (1983, J Exp Med 158:121 1).

Anti-PDE_XIV antibodies are useful for the diagnosis of inflammation, conditions associated with proliferation of hematopoietic cells and HIV infection or other disorders or diseases characterised by abnormal expression of a PDE_XIV. Diagnostic assays for a PDE_XIV include methods utilising the antibody and a label to detect a PDE_XIV polypeptide in human body fluids, cells, tissues or sections or extracts of such tissues.

The polypeptides and antibodies of the present invention may be used with or without modification. Frequently, the polypeptides and antibodies will be labelled by joining them, either covalently or noncovalently, with a reporter molecule. A wide variety of reporter molecules are known to those of skill in the art.

Antibodies may be used in method of detecting polypeptides of the invention present in biological samples by a method which comprises: (a) providing an antibody of the invention; (b) incubating a biological sample with said antibody under conditions which allow for the formation of an antibody-antigen complex; and (c) determining whether antibody-antigen complex comprising said antibody is formed.

Depending on the circumstances, suitable samples may include extracts tissues such as brain, breast, ovary, lung, colon, pancreas, testes, liver, muscle and bone tissues or from neoplastic growths derived from such tissues.

Antibodies of the invention may be bound to a solid support and/or packaged into kits in a suitable container along with suitable reagents, controls, instructions and the like.

Assays/Identification Methods

The present invention also relates to an assay method for detecting the presence of PDE_XIV in cells (such as human cells) comprising: (a) performing a reverse transcriptase-polymerase chain reaction on RNA (such as total RNA) from such cells using a pair of polymerase chain reaction primers that are specific for PDE_XIV, as determined from the DNA sequence of any one of the sequences shown in the attached sequence listings or an allelic variation thereof; and (b) assaying the appearance of an appropriately sized PCR (polymerase chain reaction) fragment—such as by agarose gel electrophoresis.

The present invention also relates to a method of identifying agents (such as compounds, other substances or compositions comprising same) that affect (such as inhibit or otherwise modify) the activity of PDE_XIV and/or the expression thereof, the method comprising contacting PDE_XIV or the nucleotide sequence coding for same with the agent and then measuring the activity of PDE_XIV and/or the expression thereof.

The present invention also relates to a method of identifying agents (such as compounds, other substances or compositions comprising same) that selectively affect (such as inhibit or otherwise modify) the activity of PDE_XIV and/or the expression thereof, the method comprising contacting PDE_XIV or the nucleotide sequence coding for same with the agent and then measuring the activity of PDE_XIV and/or the expression thereof.

The present invention also relates to a method of identifying agents (such as compounds, other substances or compositions comprising same) that selectively affect (such as inhibit or otherwise modify) the activity of PDE_XIVA1 or PDE_XIVA2 or PDE_XIVA3 or PDE_XIVA4 and/or the expression thereof, the method comprising contacting the relevant PDE_XIV or the nucleotide sequence coding for same with the agent and then measuring the activity of the relevant PDE_XIV and/or the expression thereof.

The present invention also relates to a method of identifying agents (such as compounds, other substances or compositions comprising same) that affect (such as inhibit or otherwise modify) the activity of PDE_XIV and/or the expression thereof, the method comprising measuring the activity of PDE_XIV and/or the expression thereof in the presence of the agent or after the addition of the agent in: (a) a cell line into which has been incorporated recombinant DNA comprising the DNA sequence of any one of the sequences shown in the attached sequence listings or an allelic variation thereof, or (b) a cell population or cell line that naturally selectively expresses PDE_XIV. Preferably, the activity of PDE_XIV is determined by the assay method described above.

The present invention also relates to a method of identifying agents (such as compounds, other substances or compositions comprising same) that selectively affect (such as inhibit or otherwise modify) the activity of PDE_XIV and/or the expression thereof, the method comprising measuring the activity of PDE_XIV and/or the expression thereof in the presence of the agent or after the addition of the agent in: (a) a cell line into which has been incorporated recombinant DNA comprising the DNA sequence of any one of the sequences shown in the attached sequence listings or an allelic variation thereof, or (b) a cell population or cell line that naturally selectively expresses PDE_XIV. Preferably, the activity of PDE_XIV is determined by the assay method described above.

The present invention also relates to a method of identifying agents (such as compounds, other substances or compositions comprising same) that selectively affect (such as inhibit or otherwise modify) the activity of PDE_XIVA1 or PDE_XIVA2 or PDE_XIVA3 or PDE_XIVA4 and/or the expression thereof, the method comprising measuring the activity of the respective PDE_XIV and/or the expression thereof in the presence of the agent or after the addition of the agent in: (a) a cell line into which has been incorporated recombinant DNA comprising the respective DNA sequence of any one of the sequences shown in the attached sequence listings or an allelic variation thereof, or (b) a cell population or cell line that naturally selectively expresses the respective PDE_XIV. Preferably, the activity of PDE_XIV is determined by the assay method described above.

The present invention also provides a method of screening an agent for modulation (preferably for specific modulation) of PDE_XIV (or a derivative, homologue, variant or fragment thereof) activity or the expression of the nucleotide sequence coding for same (including a derivative, homologue, variant or fragment thereof), the method comprising the steps of: a) providing a candidate agent; b) combining PDE_XIV (or the derivative, homologue, variant or fragment thereof) or the nucleotide sequence coding for same (or the derivative, homologue, variant or fragment thereof) with the candidate agent for a time sufficient to allow modulation under suitable conditions; and c) detecting modulation of the candidate agent to PDE_XIV (or the derivative, homologue, variant or fragment thereof) or the nucleotide sequence coding for same (or the derivative, homologue, variant or fragment thereof) in order to ascertain if the candidate agent modulates PDE_XIV (or the derivative, homologue, variant or fragment thereof) activity or the expression of the nucleotide sequence coding for same (or the derivative, homologue, variant or fragment thereof).

The present invention also provides a method of screening an agent for specific binding affinity with PDE_XIV (or a derivative, homologue, variant or fragment thereof) or the nucleotide sequence coding for same (including a derivative, homologue, variant or fragment thereof), the method comprising the steps of: a) providing a candidate agent; b) combining PDE_XIV (or the derivative, homologue, variant or fragment thereof) or the nucleotide sequence coding for same (or the derivative, homologue, variant or fragment thereof) with the candidate agent for a time sufficient to allow binding under suitable conditions; and c) detecting binding of the candidate agent to PDE_XIV (or the derivative, homologue, variant or fragment thereof) or the nucleotide sequence coding for same (or the derivative, homologue, variant or fragment thereof) in order to ascertain if the candidate agent binds to PDE_XIV (or the derivative, homologue, variant or fragment thereof) or the nucleotide sequence coding for same (or the derivative, homologue, variant or fragment thereof).

The present invention also provides a method of identifying an agent which is capable of modulating PDE_XIV, the method comprising the steps of: a) contacting the agent with PDE_XIV (or a derivative, homologue, variant or fragment thereof) or the nucleotide sequence coding for same (or the derivative, homologue, variant or fragment thereof), b) incubating the mixture of step a) with a cyclic nucleotide under conditions suitable for the hydrolysis of the cyclic nucleotide, c) measuring the amount of cyclic nucleotide hydrolysis, and d) comparing the amount of cyclic nucleotide hydrolysis of step c) with the amount of cyclic nucleotide hydrolysis obtained with PDE_XIV (or the derivative, homologue, variant or fragment thereof) or the nucleotide sequence coding for same (or the derivative, homologue, variant or fragment thereof) incubated without the compound, thereby determining whether the agent affects (such as stimulates or inhibits) cyclic nucleotide hydrolysis.

Thus, in certain embodiments of the present invention, PDE_XIV or a variant, homologue, fragment or derivative thereof and/or a cell line that expresses the PDE_XIV or variant, homologue, fragment or derivative thereof may be used to screen for antibodies, peptides, or other agent, such as organic or inorganic molecules, that act as modulators of phosphodiesterase activity or for the expression thereof, thereby identifying a therapeutic agent capable of modulating cyclic nucleotide levels. For example, anti-PDE_XIV antibodies capable of neutralising the activity of PDE_XIV may be used to inhibit PDE_XIV hydrolysis of cyclic nucleotides, thereby increasing their levels. Alternatively, screening of peptide libraries or organic libraries made by combinatorial chemistry with recombinantly expressed PDE_XIV or a variant, homologue, fragment or derivative thereof or cell lines expressing PDE_XIV or a variant, homologue, fragment or derivative thereof may be useful for identification of therapeutic agents that function by modulating PDE_XIV hydrolysis of cyclic nucleotides. Synthetic compounds, natural products, and other sources of potentially biologically active materials can be screened in a number of ways deemed to be routine to those of skill in the art. For example, nucleotide sequences encoding the N-terminal region of PDE_XIV may be expressed in a cell line which can be used for screening of allosteric modulators, either agonists or antagonists, of PDE_XIV activity. Alternatively, nucleotide sequences encoding the conserved catalytic domain of PDE_XIV can be expressed in cell lines and used to screen for inhibitors of cyclic nucleotide hydrolysis.

The ability of a test agent to interfere with PDE_XIV activity or cyclic nucleotide hydrolysis may be determined by measuring PDE_XIV levels or cyclic nucleotide levels (as disclosed in Smith et al 1993 Appl. Biochem. Biotechnol. 41:189–218). There are also commercially available immunoassay kits for the measurement of cAMP and cGMP (eg Amersham International, Arlington Heights, Ill. and DuPont, Boston, Mass.). The activity of PDE_XIV may also be monitored by measuring other responses such as phosphorylation or dephosphorylation of other proteins using conventional techniques developed for these purpose.

Accordingly, the present invention provides a method of identifying a compound which is capable of modulating the cyclic nucleotide phosphodiesterase activity of a PDE_XIV, or a variant, homologue, fragment or derivative thereof, comprising the steps of a) contacting the compound with a PDE_XIV, or a variant, homologue, fragment or derivative thereof; b) incubating the mixture of step a) with a cyclic nucleotide under conditions suitable for the hydrolysis of the cyclic nucleotide; c) measuring the amount of cyclic nucleotide hydrolysis; and d) comparing the amount of cyclic nucleotide hydrolysis of step c) with the amount of cyclic nucleotide hydrolysis obtained with the PDE_XIV, or a variant, homologue, fragment or derivative thereof, incubated without the compound, thereby determining whether the compound stimulates or inhibits cyclic nucleotide hydrolysis. In one embodiment of the method, the fragment may be from the N-terminal region of the PDE_XIV and provides a method to identify allosteric modulators of the PDE_XIV. In another embodiment of the present invention, the fragment may be from the carboxy terminal region of the PDE_XIV and provides a method to identify inhibitors of cyclic nucleotide hydrolysis.

A PDE_XIV polypeptide, its immunogenic fragments or oligopeptides thereof can be used for screening therapeutic compounds in any of a variety of drug screening techniques. The polypeptide employed in such a test may be free in solution, affixed to a solid support, borne on a cell surface, or located intracellularly. The abolition of activity or the formation of binding complexes between a PDE_XIV polypeptide and the agent being tested may be measured.

Accordingly, the present invention provides a method for screening one or a plurality of compounds for modulation (preferably specific modulation, such as specific binding affinity) of PDE_XIV or the expression thereof, or a portion thereof or variant, homologue, fragment or derivative thereof, comprising providing one or a plurality of compounds; combining a PDE_XIV or a nucleotide sequence coding for same or a portion thereof or variant, homologue, fragment or derivative thereof with the or each of a plurality of compounds for a time sufficient to allow modulation under suitable conditions; and detecting binding of a PDE_XIV, or portion thereof or variant, homologue, fragment or derivative thereof, to each of the plurality of compounds, thereby identifying the compound or compounds which modulate a PDE_XIV or a nucleotide sequence coding for same. In such an assay, the plurality of compounds may be produced by combinatorial chemistry techniques known to those of skill in the art.

Another technique for drug screening provides for high throughput screening of compounds having suitable binding affinity to the PDE_XIV polypeptides and is based upon the method described in detail in Geysen, European Patent Application 84/03564, published on Sep. 13, 1984. In summary, large numbers of different small peptide test compounds are synthesized on a solid substrate, such as plastic pins or some other surface. The peptide test compounds are reacted with PDE_XIV fragments and washed. A bound PDE_XIV is then detected—such as by appropriately adapting methods well known in the art. A purified PDE_XIV can also be coated directly onto plates for use in the aforementioned drug screening techniques. Alternatively, non-neutralising antibodies can be used to capture the peptide and immobilise it on a solid support.

This invention also contemplates the use of competitive drug screening assays in which neutralising antibodies capable of binding a PDE XIV specifically compete with a test compound for binding a PDE_XIV. In this manner, the antibodies can be used to detect the presence of any peptide which shares one or more antigenic determinants with a PDE_XIV.

The assay method of the present invention may be a high throughput screen (HTS). In this regard, the teachings of WO 84/03564 may be adapted for the PDE of the present invention.

The teachings of U.S. Pat. No. 5,738,985 may be adapted for the assay method of the present invention.

Agents

The present invention also provides one or more agents identified by the assays methods and identification methods of the present invention.

The agent of the present invention can be, for example, an organic compound or an inorganic compound. The agent can be, for example, a nucleotide sequence that is anti-sense to all or part of the sequences shown in the attached sequence listings.

The invention further provides an agent of the present invention (or even a pharmaceutically acceptable salt thereof, or a pharmaceutically acceptable solvate thereof) or a pharmaceutical composition containing any of the foregoing, for use as a medicament.

The present invention also provides the use of an agent to affect PDE_XIV activity (such as to inhibit, modulate or agonise) in any one or more of the putamen, the Caudate nucleus of the brain, the Occipital lobe of the brain, the heart, ovary, the pituitary gland, kidney, liver, small intestine, thymus, skeletal muscle, leukocyte regions, dorsal root ganglia, uterus, cochlea, small intestine (duodenum), astrocytoma, and appendix.

Diagnostics

The present invention also provides a diagnostic composition for the detection of PDE_XIV polynucleotide sequences. The diagnostic composition may comprise any one of the sequences shown in the attached sequence listings or a variant, homologue, fragment or derivative thereof, or a sequence capable of hybridising to all or part of any one of the sequences shown in the attached sequence listings or an allelic variation thereof.

In order to provide a basis for the diagnosis of disease, normal or standard values from a PDE_XIV polypeptide expression should be established. This is accomplished by combining body fluids or cell extracts taken from normal subjects, either animal or human, with antibody to a PDE_XIV polypeptide under conditions suitable for complex formation which are well known in the art. The amount of standard complex formation may be quantified by comparing it to a dilution series of positive controls where a known amount of antibody is combined with known concentrations of a purified PDE_XIV polypeptide. Then, standard values obtained from normal samples may be compared with values obtained from samples from subjects potentially affected by a disorder or disease related to a PDE_XIV polypeptide expression. Deviation between standard and subject values establishes the presence of the disease state.

A PDE_XIV polynucleotide, or any part thereof, may provide the basis for a diagnostic and/or a therapeutic compound. For diagnostic purposes, PDE_XIV polynucleotide sequences may be used to detect and quantify gene expression in conditions, disorders or diseases in which PDE_XIV activity may be implicated.

PDE_XIV encoding polynucleotide sequence may be used for the diagnosis of diseases resulting from expression of PDE_XIV. For example, polynucleotide sequences encoding PDE_XIV may be used in hybridisation or PCR assays of tissues from biopsies or autopsies or biological fluids, such as serum, synovial fluid or tumour biopsy, to detect abnormalities in PDE_XIV expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for PDE expression should be established. This is accomplished by combining body fluids or cell extracts taken from normal subjects, either animal or human, with PDE_XIV or a portion thereof, under conditions suitable for hybridisation or amplification. Standard hybridisation may be quantified by comparing the values obtained for normal subjects with a dilution series of positive controls run in the same experiment where a known amount of purified PDE_XIV is used. Standard values obtained from normal samples may be compared with values obtained from samples from subjects potentially affected by a disorder or disease related to expression of the PDE coding sequence. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

Thus, the present invention relates to the use of a PDE_XIV polypeptide, or variant, homologue, fragment or derivative thereof, to produce anti-PDE_XIV antibodies which can, for example, be used diagnostically to detect and quantify PDE_XIV levels in disease states.

The present invention further provides diagnostic assays and kits for the detection of PDE_XIV in cells and tissues comprising a purified PDE_XIV which may be used as a positive control, and anti-PDE_XIV antibodies. Such antibodies may be used in solution-based, membrane-based, or tissue-based technologies to detect any disease state or condition related to the expression of PDE_XIV protein or expression of deletions or a variant, homologue, fragment or derivative thereof.

Probes

Another aspect of the subject invention is the provision of nucleic acid hybridisation or PCR probes which are capable of detecting polynucleotide sequences, including genomic sequences, encoding PDE coding region or closely related molecules, such as alleles. The specificity of the probe, i.e., whether it is derived from a highly conserved, conserved or non-conserved region or domain, and the stringency of the hybridisation or amplification (high, intermediate or low) will determine whether the probe identifies only naturally occurring PDE coding sequence, or related sequences. Probes for the detection of related nucleic acid sequences are selected from conserved or highly conserved nucleotide regions of cyclic nucleotide PDE family members, such as the 3' region, and such probes may be used in a pool of degenerate probes. For the detection of identical nucleic acid sequences, or where maximum specificity is desired, nucleic acid probes are selected from the non-conserved nucleotide regions or unique regions of PDE polynucleotides. As used herein, the term "non-conserved nucleotide region" refers to a nucleotide region that is unique to the PDE coding sequence disclosed herein and does not occur in related family members, such as known cyclic nucleotide PDEs.

PCR as described in U.S. Pat. No. 4,683,195, U.S. Pat. No. 4,800,195 and U.S. Pat. No. 4,965,188 provides additional uses for oligonucleotides based upon the PDE_XIV sequence. Such oligomers are generally chemically synthesized, but they may be generated enzymatically or produced from a recombinant source. Oligomers generally comprise two nucleotide sequences, one with sense orientation (5'→3') and one with antisense (3'←5') employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

The nucleic acid sequence for PDE_XIV can also be used to generate hybridisation probes as previously described, for mapping the endogenous genomic sequence. The sequence may be mapped to a particular chromosome or to a specific region of the chromosome using well known techniques. These include in situ hybridisation to chromosomal spreads (Verma et al (1988) Human Chromosomes: A Manual of Basic Techniques, Pergamon Press, New York City), flow-sorted chromosomal preparations, or artificial chromosome constructions such as YACs, bacterial artificial chromosomes (BACs), bacterial PI constructions or single chromosome cDNA libraries.

In situ hybridisation of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localised by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc between normal, carrier or affected individuals.

Pharmaceuticals

The present invention also provides a pharmaceutical composition for treating an individual in need of same due to PDE_XIV activity, the composition comprising a therapeutically effective amount of an agent that affects (such as inhibits) said activity and a pharmaceutically acceptable carrier, diluent, excipient or adjuvant.

Thus, the present invention also covers pharmaceutical compositions comprising the agents of the present invention (an agent capable of modulating the expression pattern of the nucleotide sequence of the present invention or the activity of the expression product thereof and/or an agent identified by an assay according to the present invention). In this regard, and in particular for human therapy, even though the agents of the present invention can be administered alone, they will generally be administered in admixture with a pharmaceutical carrier, excipient or diluent selected with regard to the intended route of administration and standard pharmaceutical practice.

By way of example, in the pharmaceutical compositions of the present invention, the agents of the present invention may be admixed with any suitable binder(s), lubricant(s), suspending agent(s), coating agent(s), or solubilising agent(s).

In general, a therapeutically effective daily oral or intravenous dose of the agents of the present invention is likely to range from 0.01 to 50 mg/kg body weight of the subject to be treated, preferably 0.1 to 20 mg/kg. The agents of the present invention may also be administered by intravenous infusion, at a dose which is likely to range from 0.001–10 mg/kg/hr.

Tablets or capsules of the agents may be administered singly or two or more at a time, as appropriate. It is also possible to administer the agents of the present invention in sustained release formulations.

Thus, the present invention also provides a method of treating an individual in need of same due to PDE_XIV activity comprising administering to said individual an effective amount of the pharmaceutical composition of the present invention.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the agents of the present invention may typically be from 10 to 500 mg (in single or divided doses). Thus, and by way of example, tablets or capsules may contain from 5 to 100 mg of active agent for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

In some applications, generally, in humans, oral administration of the agents of the present invention is the preferred route, being the most convenient and can in some cases avoid disadvantages associated with other routes of administration—such as those associated with intracavernosal (i.c.) administration. In circumstances where the recipient suffers from a swallowing disorder or from impairment of drug absorption after oral administration, the drug may be administered parenterally, e.g. sublingually or buccally.

For veterinary use, the agent of the present invention is typically administered as a suitably acceptable formulation in accordance with normal veterinary practice and the veterinary surgeon will determine the dosing regimen and route of administration which will be most appropriate for a particular animal. However, as with human treatment, it may be possible to administer the agent alone for veterinary treatments.

Typically, the pharmaceutical compositions—which may be for human or animal usage—will comprise any one or more of a pharmaceutically acceptable diluent, carrier, excipient or adjuvant. The choice of pharmaceutical carrier, excipient or diluent can be selected with regard to the intended route of administration and standard pharmaceutical practice. As indicated above, the pharmaceutical compositions may comprise as—or in addition to—the carrier, excipient or diluent any suitable binder(s), lubricant(s), suspending agent(s), coating agent(s), solubilising agent(s).

In some embodiments of the present invention, the pharmaceutical compositions will comprise one or more of: an agent that has been screened by an assay of the present invention; an agent that is capable of interacting with any one of the sequences shown in the attached sequence listings including derivatives, fragments, homologues or variants thereof or sequences capable of hybridising to any one of the sequences shown in the attached sequence listings.

Included in the scope of the invention are oligonucleotide sequences, antisense RNA and DNA molecules and ribozymes, which function to destabilise PDE_XIV mRNA or inhibit translation of a PDE_XIV. Such nucleotide sequences may be used in conditions where it would be preferable to increase cyclic nucleotide levels, such as in inflammation.

A PDE_XIV antisense molecule may provide the basis for treatment of various abnormal conditions related to, for example, increased PDE_XIV activity.

A PDE_XIV nucleic acid antisense molecule may be used to block the activity of the PDE_XIV in conditions where it would be preferable to elevate cyclic nucleotide levels.

Expression vectors derived from retroviruses, adenovirus, herpes or vaccinia viruses, or from various bacterial plasmids, may be used for delivery of recombinant PDE_XIV sense or antisense molecules to the targeted cell population. Methods which are well known to those skilled in the art can be used to construct recombinant vectors containing PDE_XIV. Alternatively, recombinant PDE_XIV can be delivered to target cells in liposomes.

The full length cDNA sequence and/or its regulatory elements enable researchers to use PDE_XIV as a tool in sense (Youssoufian H and H F Lodish 1993 Mol Cell Biol 13:98–104) or antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions. Appropriate oligonucleotides, which can be 20 nucleotides in length, may be used to isolate PDE_XIV sequences or closely related molecules from human libraries.

Additionally, PDE_XIV expression can be modulated by transfecting a cell or tissue with expression vectors which express high levels of a PDE_XIV fragment in conditions where it would be preferable to block phosphodiesterase activity thereby increasing cyclic nucleotide levels. Such constructs can flood cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector and even longer if appropriate replication elements are part of the vector system.

Modifications of gene expression can be obtained by designing antisense sequences to the control regions of the PDE gene, such as the promoters, enhancers, and introns.

Oligonucleotides derived from the transcription initiation site, e.g., between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Thus the invention provides a pharmaceutical composition comprising an agent of the present invention (or even a pharmaceutically acceptable salt thereof, or a pharmaceutically acceptable solvate thereof) together with a pharmaceutically acceptable diluent, excipient or carrier.

The pharmaceutical composition could be for veterinary (i.e. animal) usage or for human usage.

Thus, the present invention therefore also relates to pharmaceutical compositions comprising effective amounts of inhibitors or antagonists of PDE_XIV protein (including anti-sense nucleic acid sequences) in admixture with a pharmaceutically acceptable diluent, carrier, excipient or adjuvant (including combinations thereof).

The present invention relates to pharmaceutical compositions which may comprise all or portions of PDE_XIV polynucleotide sequences, PDE_XIV antisense molecules, PDE_XIV polypeptides, protein, peptide or organic modulators of PDE_XIV bioactivity, such as inhibitors, antagonists (including antibodies) or agonists, alone or in combination with at least one other agent, such as stabilising compound, and may be administered in any sterile, biocompatible pharmaceutical carrier, including, but not limited to, saline, buffered saline, dextrose, and water.

General Methodology References

Although in general the techniques mentioned herein are well known in the art, reference may be made in particular to Sambrook et al., Molecular Cloning, A Laboratory Manual (1989) and Ausubel et al., Short Protocols in Molecular Biology (1999) 4$^{th}$ Ed, John Wiley & Sons, Inc. PCR is described in U.S. Pat. No. 4,683,195, U.S. Pat. No. 4,800,195 and U.S. Pat. No. 4,965,188.

Deposits

The following samples were deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on 18 Dec. 1998:

*E. coli* pHS-PDE_XIV NCIMB number NCIMB 40995

*E. coli* pMM-PDE_XIV NCIMB number NCIMB 40996

The following sample was deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on 9 Sep. 1999:

NCIMB number NCIMB 41027 is *E. coli* pHS-PDE_XIVhm

The present invention also encompasses sequences derivable and/or expressable from those deposits and embodiments comprising the same. The present invention also encompasses partial sequences derivable and/or expressable from those deposits and embodiments comprising the same, wherein those partial sequences code for active enzymatic sites. The present invention also encompasses proteins comprising sequences derivable and/or expressable from those deposits and embodiments comprising the same. The present invention also encompasses proteins comprising partial sequences derivable and/or expressable from those deposits and embodiments comprising the same, wherein those partial sequences code for active enzymatic sites.

The present invention also encompasses sequences derivable and/or expressable from those deposits and embodiments comprising the same.

INTRODUCTION TO THE EXAMPLES SECTION AND THE FIGURES

The present invention will now be described, by way of example only, with reference to the accompanying drawings in which:

FIG. 1 which presents a photographic image

Figure 2:
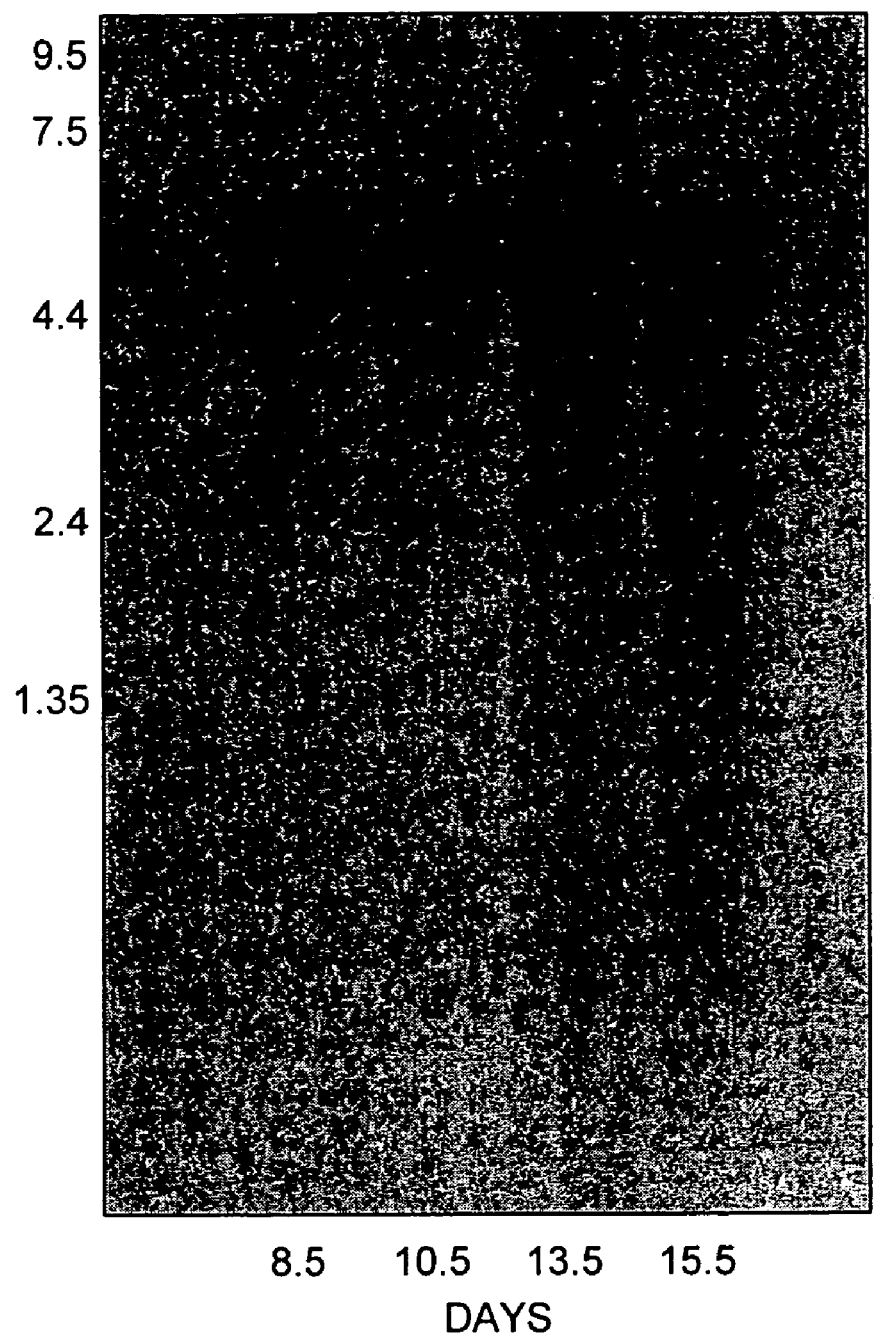

FIG. 2 which presents a photographic image;

FIG. 3 which presents a Table and a photographic image;

FIG. 4 which presents an alignment of nucleotide sequences (here the human sequence is a truncated sequence);

FIG. 5 which presents an alignment of protein sequences (here the human sequence is a truncated sequence); and FIG. 6 which presents a graph.

EXAMPLES

Northern Hybridisation and Probe Preparation

Northern blots, obtained from Clontech, were prehybridised for 1 hour in ExpressHyb hybridisation solution (Clontech) at 55° C. before a radiolabelled PDE_XIV fragment (DNA was labelled using the Megaprime random labelling system (Amersham) strictly following the manufacturers instructions with 50 uCi of $^{32}$P-dATP) was added to fresh Expresshyb and hybridised to the blot overnight at 55° C., with gentle shaking. Blots were then washed 3× at room temperature for 10 minutes each in 2×SSC (150 mM NaCl, 30 mM Na.citrate) followed by 2 washes in 0.2×SSC (15 mM NaCl, 3 mM Na.citrate) at 55° C. for 20 minutes each. Blots were then exposed to autoradiographic film.

Polymerase Chain Reactions (PCR)

PCRs were performed using standard reagents and conditions. Briefly, all reaction buffers and enzymes were obtained in kit format from either Clontech (for rapid amplification of cDNA ends (RACE) reactions) or from Life technologies for standard PCR. Oligonucleotides were obtained from a commercial supplier (OSWEL DNA services) and used at a concentration of 400 nM. Reactions were performed on a MJ Research PTC-200 thermal cycler, using cycling parameters as recommended by the manufacturer of the kit being used.

The Identification of PDE_XIV.

The clone (IMAGE clone id 1364394) was obtained from Research Genetics (2130, Memorial Pkwy, SW Huntsville, Ala. 358801, USA) as a stab culture in L-agar. Bacteria from the stab culture were streaked onto a 37 mm L-agar plate in the presence of ampicillin at a concentration of 100 mg/ml. After overnight growth at 37° C. a single clone was picked, using sterile technique, into 5 ml of LB-broth containing ampicillin at a concentration of 100 mg/ml and grown at 37° C. overnight with shaking (220 rpm). Plasmid DNA was isolated from the bacteria using a standard commercially available miniprep kit (Qiagen™) and strictly following the manufacturers instructions. The isolated DNA was then subjected to full length sequencing, using standard proprietary kits and reagents and an ABI (PE Applied Biosystems Incorporated) automated sequencer.

Isolation of a Putative Full Length cDNA Clone For PDE_XIV

To facilitate the isolation of a murine full length cDNA for PDE_XIV containing the full coding region and a terminator codon, the expression of PDE_XIV was determined in a range of tissues using Northern hybridisation. These data (FIGS. 1 and 2) show that whilst the messenger RNA (length 5.5 kb), which hybridises to PDE_XIV, is present in several tissues, it is particularly highly expressed in murine brain, skeletal muscle & liver and at the following stages of embryological development, 10.5, 13.5, 15.5 days. The 13.5 day murine embryonic cDNA library was used in a cDNA positive selection method (GeneTrapper, Life Technologies, Inc.) to isolate the PDE_XIV. The method was carried out as manufacturers instructions. The original EST sequence of clone 1364394 was in the reverse orientation, therefore, design of the selection oligonucleotide needed to be identical to the coding strand running 5' to 3', this step was critical to the success of the cloning strategy. The oligonucleotide used for the selection and repair is detailed below.

To isolate the human homologue of the murine PDE_XIV, PCR primers were designed based on the known EST 1364394 sequence, (Primer 1 and Primer 2) and used to screen a panel of cDNA libraries. PCR's carried out using these primers (the PCR was set up using reagents obtained from a PCR Reagent System kit (Life Technologies) and following the manufacturers instructions, with standard cycling parameters) resulted in the generation of a fragment of the expected size, 164 bp, obtained from the human HELA cell line cDNA library (Life Technologies, Inc.), using the same selection/repair oligonucleotide (Oligo 1) the human clone was isolated.

```
Primer 1:
newPDE1 5'-ACC GCT CAG AGA TTT CAC AGC A-3'      (SEQ ID NO:25)

Primer 2:
newPDE2 5'-CCC GTC TGA CCC CTT AGT CGT A-3'      (SEQ ID NO:26)
```

Clones were selected for follow up through screening by colony PCR using the above primers and the following method. Using a sterile toothpick a single colony was picked and added to a tube containing 25 ul of 1*PCR supermix (Life Technologies, Inc) & 200 nM of primers. The tube was vortex'ed for 1 second, centrifuged for 2 seconds at 14,000× g. The tubes were then placed in a pre-warmed thermal cycler (MJ Research PTC-200 thermal cycler) 94° C. PCR was performed using the following program: 1 cycle; 94° C., 1 minute, followed by 30 cylces of: 94° C., 30 seconds, 55° C., 30 seconds, 72° C., 1 minute. PCR products were then analysed by gel electrophoresis using standard methods.

Analysis of the isolated murine clone allowed the assembly of a contiguous sequence of 2823 bp which contains an ORF of 446 residues. The full length cDNA sequence for murine PDE_XIV is presented as SEQ ID NO:7 with the translation of the largest open reading frame within this cDNA presented as SEQ ID NO:1. The coding region is presented as SEQ ID NO:2.

Analysis of the isolated human clone allowed the assembly of a contiguous sequence of 2992 bp which contains an ORF of 288 residues. The cDNA sequence for human PDE_XIV is presented as SEQ ID NO:8 with the translation of the largest open reading frame within this cDNA presented as SEQ ID NO:3. The coding region is presented as SEQ ID NO:4. This clone has been used to screen a master RNA blot (Clontech) using standard Northern bolt methods to identify the tissue distribution for this cDNA.

The results (see FIG. 3) show that the transcript is highly expressed in the putamen and Caudate nucleus of the brain, in addition to Occipital lobe of the brain, heart, ovary, pituitary gland, kidney, liver, small intestine, thymus, and appendix.

Like all mammalian phosphodiesterases sequenced to date PDE_XIV contains a conserved catalytic domain sequence of approximately 250 amino acids in the carboxylterminal half of the protein that is thought to be essential for catalytic activity. This segment comprises amino acids 108 to 413 in SEQ ID NO:1 and exhibits sequence conservation with the corresponding region of other PDE's. From the nucleotide alignment (see FIG. 4) and the protein alignment

```
Oligo 1:
Select1 5'-GGT CAC AGA ACT GCC ACT ATG GTT AAA TGT-3'     (SEQ ID NO:24)
```

(see FIG. 5) it is clear to see that the human PDE_XIV clone is truncated at the 3' end due to a premature stop codon at position 1102 bp.

Isolation of a Putative Full Length Human cDNA Clone for PDE_XIV

A human foetal brain cDNA library was purchased from Life Technologies, Inc (LTI). 100 ml of Luria Broth (10 g tryptone, 5 g yeast extract, 5 g NaCl/liter)+100 ug/ml Ampicillin was inoculated with $2.5 \times 10^9$ c.f.u of each cDNA library. Each library was grown up and prepared individually. The cultures were grown up overnight at 30° C. and plasmid DNA was prepared as described in the GeneTrapper™ protocol (LTI). Detailed methods for the positive selection of cDNA clones using GeneTrapper™ (LTI) are outlined in the kit protocols, these were followed except for the following modifications. The single stranded cDNA library was combined with 20 ng of biotinylated capture oligonucleotide and hybridised at 37° C. for 1 hour. The eluted single stranded DNA was repaired using the capture oligonucleotide as a primer for DNA polymerase extension. The repaired cDNA libraries were electroporated in to the *E. coli* strain DH10B (LTI) using the manufacturers protocol.

Cloning, Tissue Distribution and Sequence Analysis of Human PDE_XIV

To facilitate the isolation of a full length cDNA, the expression profile of PDE_XIV was determined in a range of mouse tissues using Northern hybridisation. This identified a transcript of 5.0 kb which is particularly highly expressed in the mouse embryo at 13.5 days and in the heart, brain and liver of the adult mouse. This transcript is also present at low levels in 8.5, 10.5, 15.5 day embryos and in skeletal muscle, kidney and lung of the adult. A transcript was not detected in the spleen or testis. Based on the data a 13.5 day embryo cDNA library (LTI) was used as a template to isolate the full length sequence using a positive cDNA selection technique, GeneTrapper (LTI). This was achieved by using a PDE_XIV specific oligonucleotide. A PCR was carried out and we were able to identify cDNAs which contained at least the EST fragment. Restriction endonuclease digestion identified a number of clones containing an insert of 2885 bp and full sequence analysis showed that these clones encoded an ORF of 446 amino acids with a predicted molecular mass of 51.3 kDA.

In addition, the full length human cDNA was isolated by GeneTrapper using the same specific capture oligonucleotide and a human foetal brain cDNA library as template. A number of clones were isolated containing an insert of 2653 bp and full sequence analysis identified an ORF of 450 residues with a predicted molecular mass of 51.8 kDA. Using the full length human cDNA an RNA master blot was probed. This identified that the mRNA for human PDE_XIV is highly expressed in the caudate nucleus, putamen and occipital lobe of the brain and peripherally in the heart, ovary, pituitary gland, kidney, liver, small intestine and thymus. Lower levels were observed in skeletal muscle, colon, bladder, uterus, prostate, stomach, adrenal gland, thyroid gland. The transcript was not observed in testis, spleen, pancreas, peripheral leukocytes, lymph node, bone marrow, aorta or cerebellum.

Sequence comparison of the mouse and human PDE_XIV shows that they share 91% amino acid identity. The predicted human ORF is extended by 4 amino acids, this is the result of an insertion of five amino acids at position 428 and the deletion of a single amino acid at position 441 in the mouse sequence. Furthermore, both cDNAs contain a single cAMP protein kinase phosphyorlation site at serine 45. A phylogenetic alignment of the 230 amino acid catalytic domain of PDE_XIV (amino acids 172–420) with representatives of other PDEs shows that PDE_XIV has highest homology to and clusters with PDE7A (about 70% identity). Further bioinfomatic analysis shows that this domain shares less than 50% sequence identity with the equivalent regions in the other nine known PDE sub-families and thus may indicate that PDE_XIV may be a second representative of the PDE7 family.

The PDE_XIV sequence contains two putative divalent cation binding motifs $HXXXHX_{8-20}D$ (amino acids 173–180, 213–270), which are believed to be essential for hydrolytic activity. Hence, this is further evidence that PDE_XIV encodes a functional phosphodiesterase enzyme.

Phosphodiesterase Assays on Crude Mammalian Cell Lysates

Both the murine & human PDE_XIV cDNA clones were transfected into mammalian COS7 cell line (ATCC) using Lipofectamine (Life Technologies, Inc) and standard methods. The COS7 cells were harvested 72 hr's post transfection and assayed for PDE activity using the following phosphodiesterase activity, a commercially available SPA (scintillation proximity assay) kit (Amersham) for cAMP SPA assay (Amersham). Serial dilution's of the cell lysates were made in lysis buffer (50 mM HEPES pH 7.2, 1.92 mM $MgCl_2$, 50 mM KCL, 10 mM EGTA, 1 protease inhibitor tablet/50 mls) to dilute out any endogenous inhibitory effects. To 25 ml of diluted crude lysate, 25 ml of buffer D (Buffer C+BSA @ 2 mg/ml) was added followed by 50 ml of buffer C (20 mM Tris.HCL (pH 7.4), 5 mM $MgCl_2.6H_2O$) containing 500 nM of cAMP substrate, (20 µl of [$^3$H] cAMP (1 µM. 4 µCi/ml) plus 423 µl of cold cAMP, 10 µM/5 ml). The reaction was incubated for 30 minutes at 30° C. 50 µl of SPA beads was then added, immediately centrifuged at 2000 rpm for 5 miniutes. Reading were collected on a Topcount (Wallac) scintillation counter.

The results (see FIG. 6) illustrate that both the human and murine PDE_XIV clones to be active, 10 fold higher than the mock transfected control.

Phosphodiesterase Expression in Baculovirus

PDE_XIV was expressed in Baculovirus when fused to an N-terminal FLAG-tag—details on which are presented later.

Phosphodiesterase cAMP Activity

Using cAMP Scintillation Proximity Assays on purified expressed PDE_XIV with cAMP concentrations ranging from 0–10 µM, the expressed PDE_XIV exhibited a strong cAMP activity with a Km of 0.08µM (as determined by a Hanes plot derived from the kinetic curve). Studies also revealed that the PDE_XIV has no activity against cGMP. Thus, the PDE_XIV may be cAMP specific.

Phosphodiesterase Inhibition Studies

PDE_XIV was found not to be sensitive to the PDE inhibitors milrinone, Rolipram and Ariflo. However, inhibition of PDE_XIVactivity was seen with Dipyridamole and IBMX with IC50 values of 10.72 µM and 9.32 µM respectively. The data for these studies are presented in the following Table.

| EFFECTS OF INHIBITORS ON PDEXIV | | |
|---|---|---|
| COMPOUND | SELECTIVITY | IC50 FOR PDEXIV (μM) (N = 2) |
| Dipyridamole | PDE5/6/8 (0.9/0.38/1.5 μM) | 10.72 ± 2.74 |
| IBMX | Non-selective (2–50 μM) | 9.72 ± 0.32 |
| Rolipram | PDE4 (2.0 μM) | >30 |
| Milrinone | PDE3/4 (3.2 μM/19 μM) | >30 |
| Ariflo | PDE4D (40 nM) | >30 |

Baculovirus Expression

The following studies demonstrate that the PDE enzyme of the present invention—called PDE here for short—can be generated using a baculovirus expression system.

The following studies also demonstrate that the PDE shows cyclic nucleotide hydrolytic activity when it has been expressed in the baculovirus system.

The PDE enzyme was generated using the baculovirus expression system based on *Autographa californica* nuclear polyhedrosis virus (AcNPV) infection of *Spodoptera frugiperda* insect cells (Sf9 cells).

In these studies, cDNA encoding PDE was cloned into the donor plasmid pFASTBAC-FLAG which contains a mini-Tn7 transposition element. The recombinant plasmid was transformed into DH10BAC competent cells which contain the parent bacmid bMON14272 (AcNPV infectious DNA) and a helper plasmid. The mini-Tn7 element on the pFAST-BAC donor can transpose to the attTn7 attachment site on the bacmid thus introducing the PDE gene into the viral genome. Colonies containing recombinant bacmids are identified by disruption of the lacZ gene. The PDE/bacmid construct can then be isolated and infected into insect cells (Sf9 cells) resulting in the production of infectious recombinant baculovirus particles and expression of recombinant PDE-FLAG fusion protein.

The phosphodiesterase activity of the crude cell extracts was measured.

Cells were harvested and extracts prepared 24, 48 and 72 hours after transfection.

These results confirm that PDE cDNA encodes a phosphodiesterase which is able to hydrolyse cAMP.

The crude lysate material was purified by FPLC using a column containing agarose beads (M2 affinity gel) to which a purified IgG$_1$ monoclonal anti-FLAG antibody had been conjugated by hydrazide linkage (Eastman Kodak). This allows the specific retention on the column of the recombinant material (since this is fused to the FLAG epitope) whilst the endogenous insect proteins are washed off in the eluate. The recombinant material is then washed off under conditions of low pH. This purified material was more suitable for detailed enzymatic and inhibitor studies. The purity of the material is assessed by coomassie staining after sodium dodecyl sulphate-polyacrylamide gel electrophoresis (SDS-PAGE) or through western blotting onto a nitro-cellulose membrane of an unstained SDS-PAGE (containing recombinant PDE) and analysis with the IgG1 monoclonal anti-FLAG epitope antibody. The PDE-FLAG fusion protein is detected due to the interaction between the anti-FLAG antibody and the FLAG epitope which is fused to the PDE protein.

The phosphodiesterase activity of the purified PDE-FLAG fusion protein was assayed using a commercially available SPA (scintillation proximity assay) kit (Amersham—Amersham place, Little Chalfont, Bucks, HP7 9NA UK) for either cAMP and/or cGMP hydrolytic activity. This can be used to permit the determination of the Km value for PDE against cAMP by determining the enzyme activity at a range of substrate concentrations allowing the calculation of an approximate Vmax value for the enzyme.

The results of these experiments show that the PDE cDNA encodes a phosphodiesterase which is able to hydrolyse cAMP.

SUMMARY

In summary the present invention provides and the Examples show inter alia:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of treatment based on said novel sequences.
7. Pharmaceutical compositions based on said novel sequences.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An isolated or purified PDE 7 isozyme comprising the amino acid sequence set fourth in SEQ ID NO:5, or an amino acid sequence having at least 95% homology to SEQ ID NO:5, and wherein said sequence has phosphodiesterase activity.

2. An isolated or purified amino acid sequence comprising SEQ ID NO: 5.

3. An isolated or purified amino acid sequence comprising an amino acid sequence having 95% sequence identity to SEQ ID NO: 5 and wherein said sequence has phosphodiesterase activity.

4. An isolated or purified amino acid sequence as recited in claim 3 wherein said sequence is a human sequence.

5. An isolated or purified amino acid sequence as recited in claim 3 wherein said sequence has 98% sequence identity to SEQ ID NO: 5.

6. An isolated or purified amino acid sequence as recited in claim 3, wherein said sequence has 99% sequence identity to SEQ ID NO: 5.

* * * * *